US012582819B2

(12) United States Patent
Levine et al.

(10) Patent No.: US 12,582,819 B2
(45) Date of Patent: Mar. 24, 2026

(54) TREATMENT OF INFLAMMATORY DISORDERS

(71) Applicant: SetPoint Medical Corporation, Valencia, CA (US)

(72) Inventors: Jacob A. Levine, West Hempstead, NY (US); David Chernoff, Sausalito, CA (US); Murthy V. Simhambhatla, Valencia, CA (US)

(73) Assignee: SetPoint Medical Corporation, Valencia, CA (US)

( * ) Notice: Subject to any disclaimer, the term of this patent is extended or adjusted under 35 U.S.C. 154(b) by 0 days.

(21) Appl. No.: 18/976,281

(22) Filed: Dec. 10, 2024

(65) Prior Publication Data

US 2025/0099754 A1    Mar. 27, 2025

Related U.S. Application Data

(63) Continuation of application No. 18/730,753, filed as application No. PCT/US2023/061048 on Jan. 20, 2023.

(60) Provisional application No. 63/407,588, filed on Sep. 16, 2022, provisional application No. 63/266,970, filed on Jan. 20, 2022.

(51) Int. Cl.
| | |
|---|---|
| *A61N 1/36* | (2006.01) |
| *A61N 7/00* | (2006.01) |
| *C07K 16/24* | (2006.01) |
| *C07K 16/28* | (2006.01) |

(52) U.S. Cl.
CPC ....... *A61N 1/36014* (2013.01); *A61N 1/3606* (2013.01); *A61N 7/00* (2013.01); *C07K 16/241* (2013.01); *C07K 16/2818* (2013.01); *C07K*
*16/2866* (2013.01); *C07K 16/2878* (2013.01); *C07K 16/2887* (2013.01); *C07K 2317/21* (2013.01); *C07K 2317/24* (2013.01); *C07K 2319/30* (2013.01)

(58) Field of Classification Search
CPC .... A61N 1/36014; A61N 7/00; C07K 16/241; C07K 16/2818; C07K 16/2866
USPC .......................................................... 604/20
See application file for complete search history.

(56) References Cited

U.S. PATENT DOCUMENTS

| | | | |
|---|---|---|---|
| 2,164,121 | A | 6/1939 | Pescador |
| 3,363,623 | A | 1/1968 | Atwell |
| 3,631,534 | A | 12/1971 | Hirota et al. |
| 4,073,296 | A | 2/1978 | McCall |
| 4,098,277 | A | 7/1978 | Mendell |
| 4,305,402 | A | 12/1981 | Katims |

(Continued)

FOREIGN PATENT DOCUMENTS

| | | |
|---|---|---|
| CN | 201230913 A | 5/2009 |
| CN | 101528303 A | 9/2009 |

(Continued)

OTHER PUBLICATIONS

US 6,184,239 B1, 02/2001, Puskas (withdrawn)

(Continued)

*Primary Examiner* — Phillip A Gray
(74) *Attorney, Agent, or Firm* — Shay Glenn LLP

(57) ABSTRACT

Methods and apparatuses for treating inflammatory diseases by neurostimulation in patients who have failed to adequately respond or have become intolerant to a drug therapy (such as a TNF inhibitor and/or a JAK inhibitor).

20 Claims, 7 Drawing Sheets

(56)　　　　　　References Cited

U.S. PATENT DOCUMENTS

| | | | |
|---|---|---|---|
| 4,503,863 A | 3/1985 | Katims | |
| 4,573,481 A | 3/1986 | Bullara | |
| 4,590,946 A | 5/1986 | Loeb | |
| 4,632,095 A | 12/1986 | Libin | |
| 4,649,936 A | 3/1987 | Ungar et al. | |
| 4,702,254 A | 10/1987 | Zabara | |
| 4,840,793 A | 6/1989 | Todd, III et al. | |
| 4,867,164 A | 9/1989 | Zabara | |
| 4,929,734 A | 5/1990 | Coughenour et al. | |
| 4,930,516 A | 6/1990 | Alfano et al. | |
| 4,935,234 A | 6/1990 | Todd, III et al. | |
| 4,979,511 A | 12/1990 | Terry, Jr. | |
| 4,991,578 A | 2/1991 | Cohen | |
| 5,019,648 A | 5/1991 | Schlossman et al. | |
| 5,025,807 A | 6/1991 | Zabara | |
| 5,038,781 A | 8/1991 | Lynch | |
| 5,049,659 A | 9/1991 | Cantor et al. | |
| 5,073,560 A | 12/1991 | Wu et al. | |
| 5,106,853 A | 4/1992 | Showell et al. | |
| 5,111,815 A | 5/1992 | Mower | |
| 5,154,172 A | 10/1992 | Terry, Jr. et al. | |
| 5,175,166 A | 12/1992 | Dunbar et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,203,326 A | 4/1993 | Collins | |
| 5,205,285 A | 4/1993 | Baker, Jr. | |
| 5,215,086 A | 6/1993 | Terry, Jr. et al. | |
| 5,215,089 A | 6/1993 | Baker, Jr. | |
| 5,222,494 A | 6/1993 | Baker, Jr. | |
| 5,231,988 A | 8/1993 | Wernicke et al. | |
| 5,235,980 A | 8/1993 | Varrichio et al. | |
| 5,237,991 A | 8/1993 | Baker et al. | |
| 5,251,634 A | 10/1993 | Weinberg | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,304,206 A | 4/1994 | Baker, Jr. et al. | |
| 5,330,507 A | 7/1994 | Schwartz | |
| 5,330,515 A | 7/1994 | Rutecki et al. | |
| 5,335,657 A | 8/1994 | Terry, Jr. et al. | |
| 5,344,438 A | 9/1994 | Testerman et al. | |
| 5,351,394 A | 10/1994 | Weinberg | |
| 5,403,845 A | 4/1995 | Dunbar et al. | |
| 5,458,625 A | 10/1995 | Kendall | |
| 5,472,841 A | 12/1995 | Jayasena et al. | |
| 5,487,756 A | 1/1996 | Kallesce et al. | |
| 5,496,938 A | 3/1996 | Gold et al. | |
| 5,503,978 A | 4/1996 | Schneider et al. | |
| 5,531,778 A | 7/1996 | Maschino et al. | |
| 5,540,730 A | 7/1996 | Terry, Jr. et al. | |
| 5,540,734 A | 7/1996 | Zabara | |
| 5,567,588 A | 10/1996 | Gold et al. | |
| 5,567,724 A | 10/1996 | Kelleher et al. | |
| 5,571,150 A | 11/1996 | Wernicke et al. | |
| 5,580,737 A | 12/1996 | Polisky et al. | |
| 5,582,981 A | 12/1996 | Toole et al. | |
| 5,604,231 A | 2/1997 | Smith et al. | |
| 5,607,459 A | 3/1997 | Paul et al. | |
| 5,611,350 A | 3/1997 | John | |
| 5,618,818 A | 4/1997 | Ojo et al. | |
| 5,629,285 A | 5/1997 | Black et al. | |
| 5,637,459 A | 6/1997 | Burke et al. | |
| 5,651,378 A | 7/1997 | Matheny et al. | |
| 5,654,151 A | 8/1997 | Allen et al. | |
| 5,683,867 A | 11/1997 | Biesecker et al. | |
| 5,690,681 A | 11/1997 | Geddes et al. | |
| 5,690,693 A | 11/1997 | Wang et al. | |
| 5,700,282 A | 12/1997 | Zabara | |
| 5,705,337 A | 1/1998 | Gold et al. | |
| 5,707,400 A | 1/1998 | Terry, Jr. et al. | |
| 5,709,853 A | 1/1998 | Iino et al. | |
| 5,712,375 A | 1/1998 | Jensen et al. | |
| 5,718,912 A | 2/1998 | Thompson et al. | |
| 5,726,017 A | 3/1998 | Lochrie et al. | |
| 5,726,179 A | 3/1998 | Messer, Jr. et al. | |
| 5,727,556 A | 3/1998 | Weth et al. | |
| 5,733,255 A | 3/1998 | Dinh et al. | |
| 5,741,802 A | 4/1998 | Kem et al. | |
| 5,773,598 A | 6/1998 | Burke et al. | |
| 5,786,462 A | 7/1998 | Schneider et al. | |
| 5,788,656 A | 8/1998 | Mino | |
| 5,792,210 A | 8/1998 | Wamubu et al. | |
| 5,824,027 A | 10/1998 | Hoffer et al. | |
| 5,853,005 A | 12/1998 | Scanlon | |
| 5,854,289 A | 12/1998 | Bianchi et al. | |
| 5,902,814 A | 5/1999 | Gordon et al. | |
| 5,913,876 A | 6/1999 | Taylor et al. | |
| 5,916,239 A | 6/1999 | Geddes et al. | |
| 5,919,216 A | 7/1999 | Houben et al. | |
| 5,928,272 A | 7/1999 | Adkins et al. | |
| 5,964,794 A | 10/1999 | Bolz et al. | |
| 5,977,144 A | 11/1999 | Meyer et al. | |
| 5,994,330 A | 11/1999 | El Khoury | |
| 6,002,964 A | 12/1999 | Feler et al. | |
| 6,006,134 A | 12/1999 | Hill et al. | |
| 6,017,891 A | 1/2000 | Eibl et al. | |
| 6,028,186 A | 2/2000 | Tasset et al. | |
| 6,051,017 A | 4/2000 | Loeb et al. | |
| 6,083,696 A | 7/2000 | Biesecker et al. | |
| 6,083,905 A | 7/2000 | Voorberg et al. | |
| 6,096,728 A | 8/2000 | Collins et al. | |
| 6,104,956 A | 8/2000 | Naritoku et al. | |
| 6,110,900 A | 8/2000 | Gold et al. | |
| 6,110,914 A | 8/2000 | Phillips et al. | |
| 6,117,837 A | 9/2000 | Tracey et al. | |
| 6,124,449 A | 9/2000 | Gold et al. | |
| 6,127,119 A | 10/2000 | Stephens et al. | |
| 6,140,490 A | 10/2000 | Biesecker et al. | |
| 6,141,590 A | 10/2000 | Renirie et al. | |
| 6,147,204 A | 11/2000 | Gold et al. | |
| 6,159,145 A | 12/2000 | Satoh | |
| 6,164,284 A | 12/2000 | Schulman et al. | |
| 6,166,048 A | 12/2000 | Bencherif | |
| 6,168,778 B1 | 1/2001 | Janjic et al. | |
| 6,171,795 B1 | 1/2001 | Korman et al. | |
| 6,205,359 B1 | 3/2001 | Boveja | |
| 6,208,894 B1 | 3/2001 | Schulman et al. | |
| 6,208,902 B1 | 3/2001 | Boveja | |
| 6,210,321 B1 | 4/2001 | Di Mino et al. | |
| 6,224,862 B1 | 5/2001 | Turecek et al. | |
| 6,233,488 B1 | 5/2001 | Hess | |
| 6,266,564 B1 | 7/2001 | Hill et al. | |
| 6,269,270 B1 | 7/2001 | Boveja | |
| 6,304,775 B1 | 10/2001 | Lasemidis et al. | |
| 6,308,104 B1 | 10/2001 | Taylor et al. | |
| 6,337,997 B1 | 1/2002 | Rise | |
| 6,339,725 B1 | 1/2002 | Naritoku et al. | |
| 6,341,236 B1 | 1/2002 | Osorio et al. | |
| 6,356,787 B1 | 3/2002 | Rezal et al. | |
| 6,356,788 B2 | 3/2002 | Boveja | |
| 6,381,499 B1 | 4/2002 | Taylor et al. | |
| 6,405,732 B1 | 6/2002 | Edwards et al. | |
| 6,407,095 B1 | 6/2002 | Lochead et al. | |
| 6,428,484 B1 | 8/2002 | Battmer et al. | |
| 6,429,217 B1 | 8/2002 | Puskas | |
| 6,447,443 B1 | 9/2002 | Keogh et al. | |
| 6,449,507 B1 | 9/2002 | Hill et al. | |
| 6,473,644 B1 | 10/2002 | Terry, Jr. et al. | |
| 6,479,523 B1 | 11/2002 | Puskas | |
| 6,487,446 B1 | 11/2002 | Hill et al. | |
| 6,511,500 B1 | 1/2003 | Rahme | |
| 6,528,529 B1 | 3/2003 | Brann et al. | |
| 6,532,388 B1 | 3/2003 | Hill et al. | |
| 6,542,774 B2 | 4/2003 | Hill et al. | |
| 6,556,868 B2 | 4/2003 | Naritoku et al. | |
| 6,564,102 B1 | 5/2003 | Boveja | |
| 6,587,719 B1 | 7/2003 | Barrett et al. | |
| 6,587,727 B2 | 7/2003 | Osorio et al. | |
| 6,600,956 B2 | 7/2003 | Maschino et al. | |
| 6,602,891 B2 | 8/2003 | Messer et al. | |
| 6,609,025 B2 | 8/2003 | Barrett et al. | |
| 6,610,713 B2 | 8/2003 | Tracey | |
| 6,611,715 B1 | 8/2003 | Boveja | |

(56)                References Cited

U.S. PATENT DOCUMENTS

| | | | |
|---|---|---|---|
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,474 B1 | 5/2004 | Loeb et al. |
| 6,735,475 B1 | 5/2004 | Whitehurst et al. |
| 6,760,626 B1 | 7/2004 | Boveja |
| 6,762,032 B1 | 7/2004 | Nelson et al. |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezal |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukul |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,634,315 B2 | 12/2009 | Cholette |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,869 B1 | 1/2011 | Farazi |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,504,161 B1 | 8/2013 | Kornet et al. |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 9,987,492 B2 | 6/2018 | Tracey et al. |
| 9,993,651 B2 | 6/2018 | Faltys et al. |
| 10,166,395 B2 | 1/2019 | Tracey et al. |
| 10,220,203 B2 | 3/2019 | Faltys et al. |
| 10,238,883 B2 | 3/2019 | Jacobson |
| 10,449,358 B2 | 10/2019 | Levine et al. |
| 10,561,846 B2 | 2/2020 | Tracey et al. |
| 10,583,304 B2 | 3/2020 | Faltys et al. |
| 10,596,367 B2 | 3/2020 | Faltys et al. |
| 10,695,569 B2 | 6/2020 | Levine et al. |
| 10,716,936 B2 | 7/2020 | Faltys et al. |
| 10,806,928 B2 | 10/2020 | Sharma et al. |
| 10,912,712 B2 | 2/2021 | Tracey et al. |
| 11,051,744 B2 | 7/2021 | Levine et al. |
| 11,110,287 B2 | 9/2021 | Faltys et al. |
| 11,173,307 B2 | 11/2021 | Levine et al. |

(56)          References Cited

U.S. PATENT DOCUMENTS

| | | |
|---|---|---|
| 11,207,518 B2 | 12/2021 | Huston et al. |
| 11,260,229 B2 | 3/2022 | Manogue |
| 11,278,718 B2 | 3/2022 | Faltys et al. |
| 11,311,725 B2 | 4/2022 | Levine et al. |
| 11,344,724 B2 | 5/2022 | Huston et al. |
| 11,383,091 B2 | 7/2022 | Faltys et al. |
| 11,406,833 B2 | 8/2022 | Faltys et al. |
| 11,471,681 B2 | 10/2022 | Zitnik et al. |
| 11,517,572 B2 | 12/2022 | Kirkland et al. |
| 11,547,852 B2 | 1/2023 | Levine et al. |
| 11,857,788 B2 | 1/2024 | Manogue |
| 11,890,471 B2 | 2/2024 | Levine et al. |
| 11,938,324 B2 | 3/2024 | Zanos et al. |
| 11,964,150 B2 | 4/2024 | Zitnik et al. |
| 11,969,253 B2 | 4/2024 | Levine et al. |
| 12,121,726 B2 | 10/2024 | Levine et al. |
| 12,172,017 B2 | 12/2024 | Levine et al. |
| 12,220,579 B2 | 2/2025 | Manogue |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1 | 2/2003 | Perreault et al. |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0243211 A1 | 12/2004 | Colliou et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075694 A1 | 4/2005 | Schmeling et al. |
| 2005/0075698 A1 | 4/2005 | Phillips et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |

(56) References Cited

U.S. PATENT DOCUMENTS

| | | |
|---|---|---|
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen et al. |
| 2006/0142802 A1 | 6/2006 | Armstrong |
| 2006/0142822 A1 | 6/2006 | Tulgar |
| 2006/0149337 A1 | 7/2006 | John |
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178706 A1 | 8/2006 | Lisogurski et al. |
| 2006/0190044 A1 | 8/2006 | Libbus et al. |
| 2006/0190053 A1 | 8/2006 | Dobak |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0136098 A1 | 6/2007 | Smythe et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0015659 A1 | 1/2008 | Zhang |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0166348 A1 | 7/2008 | Kupper et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234780 A1 | 9/2008 | Smith |
| 2008/0234790 A1 | 9/2008 | Bayer et al. |
| 2008/0281197 A1 | 11/2008 | Wiley et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0076561 A1 | 3/2009 | Libbus et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125076 A1 | 5/2009 | Shuros et al. |
| 2009/0125079 A1 | 5/2009 | Armstrong et al. |
| 2009/0131995 A1 | 5/2009 | Sloan et al. |
| 2009/0171405 A1 | 7/2009 | Craig |
| 2009/0177112 A1 | 7/2009 | Gharib et al. |
| 2009/0182388 A1 | 7/2009 | Von Arx et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0281594 A1 | 11/2009 | King et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |

(56) References Cited

U.S. PATENT DOCUMENTS

| | | |
|---|---|---|
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0167937 A1 | 7/2010 | Goldknopf et al. |
| 2010/0191304 A1 | 7/2010 | Scott |
| 2010/0204766 A1 | 8/2010 | Zdeblick et al. |
| 2010/0215632 A1 | 8/2010 | Boss et al. |
| 2010/0219796 A1 | 9/2010 | Kallmyer |
| 2010/0241183 A1 | 9/2010 | DiLorenzo |
| 2010/0241195 A1 | 9/2010 | Meadows et al. |
| 2010/0241207 A1 | 9/2010 | Bluger |
| 2010/0249859 A1 | 9/2010 | DiLorenzo |
| 2010/0280500 A1 | 11/2010 | Skelton et al. |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0009734 A1 | 1/2011 | Foley et al. |
| 2011/0042574 A1 | 2/2011 | Nishino et al. |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0145588 A1 | 6/2011 | Stubbs et al. |
| 2011/0152967 A1 | 6/2011 | Simon et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0276112 A1 | 11/2011 | Simon et al. |
| 2011/0301658 A1 | 12/2011 | Yoo et al. |
| 2011/0301667 A1 | 12/2011 | Olson et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0136408 A1 | 5/2012 | Grill et al. |
| 2012/0179219 A1 | 7/2012 | Kisker et al. |
| 2012/0185009 A1 | 7/2012 | Kornet et al. |
| 2012/0185020 A1 | 7/2012 | Simon et al. |
| 2012/0296176 A1 | 11/2012 | Herbst |
| 2012/0302821 A1 | 11/2012 | Burnett |
| 2013/0013016 A1 | 1/2013 | Diebold |
| 2013/0018439 A1 | 1/2013 | Chow et al. |
| 2013/0066392 A1 | 3/2013 | Simon et al. |
| 2013/0066395 A1 | 3/2013 | Simon et al. |
| 2013/0071390 A1 | 3/2013 | Stadheim et al. |
| 2013/0150756 A1 | 6/2013 | Vitek et al. |
| 2013/0238047 A1* | 9/2013 | Libbus ................. A61N 1/3702 |
| | | 607/27 |
| 2013/0245718 A1 | 9/2013 | Birkholz et al. |
| 2013/0274831 A1 | 10/2013 | Otto et al. |
| 2013/0278226 A1 | 10/2013 | Cong et al. |
| 2013/0289385 A1 | 10/2013 | Lozano et al. |
| 2013/0317580 A1 | 11/2013 | Simon et al. |
| 2014/0046407 A1 | 2/2014 | Ben-Ezra et al. |
| 2014/0070761 A1 | 3/2014 | Labbe et al. |
| 2014/0206945 A1 | 7/2014 | Liao |
| 2014/0210524 A1 | 7/2014 | Roberts |
| 2014/0213926 A1 | 7/2014 | Vaidyanathan |
| 2014/0257425 A1 | 9/2014 | Arcot-Krishnamurthy et al. |
| 2014/0277260 A1 | 9/2014 | Khalil et al. |
| 2014/0288551 A1 | 9/2014 | Bharmi et al. |
| 2014/0324118 A1 | 10/2014 | Simon et al. |
| 2014/0330335 A1 | 11/2014 | Errico et al. |
| 2014/0336730 A1 | 11/2014 | Simon et al. |
| 2014/0371818 A1 | 12/2014 | Bond et al. |
| 2015/0018728 A1 | 1/2015 | Gross et al. |
| 2015/0031064 A1 | 1/2015 | Bilello et al. |
| 2015/0119956 A1 | 4/2015 | Libbus et al. |
| 2015/0133717 A1 | 5/2015 | Ghiron et al. |
| 2015/0180271 A1 | 6/2015 | Angara et al. |
| 2015/0196767 A1 | 7/2015 | Ahmed |
| 2015/0202446 A1 | 7/2015 | Franke et al. |
| 2015/0233904 A1 | 8/2015 | Nayak |
| 2015/0241447 A1 | 8/2015 | Zitnik et al. |
| 2016/0038745 A1* | 2/2016 | Faltys ................. A61N 1/37205 |
| | | 607/60 |
| 2016/0089540 A1 | 3/2016 | Bolea |
| 2016/0096016 A1* | 4/2016 | Tracey ................... A61N 1/327 |
| | | 604/20 |
| 2016/0250097 A9 | 9/2016 | Tracey et al. |
| 2016/0279435 A1 | 9/2016 | Hyde et al. |
| 2016/0331952 A1 | 11/2016 | Faltys et al. |
| 2016/0367808 A9 | 12/2016 | Simon et al. |
| 2016/0367809 A1 | 12/2016 | Patel et al. |
| 2017/0189699 A1 | 7/2017 | Dellamano et al. |
| 2017/0202467 A1 | 7/2017 | Zitnik et al. |
| 2017/0239484 A1 | 8/2017 | Ram Rakhyani et al. |
| 2017/0245379 A1 | 8/2017 | Kang |
| 2017/0254818 A1 | 9/2017 | Haskins et al. |
| 2017/0304621 A1 | 10/2017 | Malbert et al. |
| 2017/0361093 A1 | 12/2017 | Yoo et al. |
| 2018/0021580 A1 | 1/2018 | Tracey et al. |
| 2018/0078769 A1 | 3/2018 | Dinsmoor et al. |
| 2018/0085578 A1 | 3/2018 | Rennaker, II et al. |
| 2018/0117319 A1 | 5/2018 | Chew et al. |
| 2018/0117320 A1 | 5/2018 | Levine et al. |
| 2018/0133460 A1 | 5/2018 | Townley et al. |
| 2018/0207450 A1 | 7/2018 | Sanchez et al. |
| 2018/0289970 A1 | 10/2018 | Faltys et al. |
| 2019/0010535 A1 | 1/2019 | Pujol Onofre et al. |
| 2019/0022389 A1 | 1/2019 | Leonhardt |
| 2019/0030334 A1 | 1/2019 | Lerman et al. |
| 2019/0054295 A1 | 2/2019 | Pannu et al. |
| 2019/0090358 A1 | 3/2019 | Aresta et al. |
| 2019/0111263 A1 | 4/2019 | Levine et al. |
| 2019/0192847 A1 | 6/2019 | Faltys et al. |
| 2019/0209844 A1 | 7/2019 | Estellar et al. |
| 2019/0240490 A1* | 8/2019 | Yeh ..................... A61N 1/0551 |
| 2019/0290902 A1 | 9/2019 | Romero-Ortega et al. |
| 2019/0358461 A1 | 11/2019 | Steinke |
| 2020/0078589 A1 | 3/2020 | Simon et al. |
| 2020/0171312 A1 | 6/2020 | Dinsmoor et al. |
| 2020/0261722 A1 | 8/2020 | Alataris et al. |
| 2020/0384259 A1 | 12/2020 | Chasensky et al. |
| 2020/0402656 A1 | 12/2020 | DeBates et al. |
| 2021/0121696 A1 | 4/2021 | Parker et al. |
| 2021/0251848 A1 | 8/2021 | Tracey et al. |
| 2021/0353949 A1 | 11/2021 | Faltys et al. |
| 2022/0118257 A1 | 4/2022 | Huston et al. |
| 2022/0189604 A1 | 6/2022 | El-Khatib et al. |
| 2022/0193413 A1 | 6/2022 | Levine et al. |
| 2022/0212001 A1 | 7/2022 | Faltys et al. |
| 2022/0257941 A1 | 8/2022 | Levine et al. |
| 2022/0280797 A1 | 9/2022 | Faltys et al. |
| 2023/0019961 A1 | 1/2023 | Huston et al. |
| 2023/0241387 A1 | 8/2023 | Levine et al. |
| 2023/0321445 A1 | 10/2023 | Zanos et al. |
| 2024/0042201 A1 | 2/2024 | Huston et al. |
| 2024/0215900 A1 | 7/2024 | Levine et al. |
| 2024/0216688 A1 | 7/2024 | Zitnik et al. |
| 2024/0242825 A1 | 7/2024 | Calle et al. |
| 2024/0299745 A1 | 9/2024 | Levine et al. |
| 2024/0307688 A1 | 9/2024 | Levine |
| 2024/0342474 A1 | 10/2024 | Levine et al. |
| 2024/0350807 A1 | 10/2024 | Li et al. |
| 2025/0144423 A1 | 5/2025 | Manogue |
| 2025/0161682 A1 | 5/2025 | Zitnik et al. |
| 2025/0161699 A1 | 5/2025 | Faltys et al. |
| 2025/0170391 A1 | 5/2025 | Faltys et al. |
| 2025/0276177 A1 | 9/2025 | Levine et al. |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| CN | 104602759 A | 5/2015 |
| CN | 106794347 A | 5/2017 |
| CN | 107510899 A | 12/2017 |
| CN | 107666937 A | 2/2018 |
| DE | 2628045 A1 | 1/1977 |
| DE | 3736664 A1 | 5/1989 |

(56) References Cited

FOREIGN PATENT DOCUMENTS

| | | | |
|---|---|---|---|
| DE | 20316509 U1 | 4/2004 | |
| EP | 0438510 B1 | 8/1996 | |
| EP | 0726791 B1 | 6/2000 | |
| EP | 1001827 B1 | 1/2004 | |
| EP | 2213330 A2 | 8/2010 | |
| EP | 2073896 B1 | 10/2011 | |
| EP | 3470111 A1 | 4/2019 | |
| GB | 04133 A.D. 1909 | 2/1910 | |
| GB | 2073428 A | 10/1981 | |
| JP | 2017502787 | 1/2017 | |
| JP | 2019517830 | 6/2019 | |
| KR | 20050039445 A | 4/2005 | |
| WO | WO93/01862 A1 | 2/1993 | |
| WO | WO97/30998 A1 | 8/1997 | |
| WO | WO98/20868 A1 | 5/1998 | |
| WO | WO00/27381 A2 | 5/2000 | |
| WO | WO00/47104 A2 | 8/2000 | |
| WO | WO01/00273 A1 | 1/2001 | |
| WO | WO01/08617 A1 | 2/2001 | |
| WO | WO01/89526 A1 | 11/2001 | |
| WO | WO02/44176 A1 | 6/2002 | |
| WO | WO02/057275 A1 | 7/2002 | |
| WO | WO03/072135 A2 | 9/2003 | |
| WO | WO2004/000413 A2 | 12/2003 | |
| WO | WO2004/064918 A1 | 8/2004 | |
| WO | WO2006/073484 A1 | 7/2006 | |
| WO | WO2006/076681 A2 | 7/2006 | |
| WO | WO2007/133718 A2 | 11/2007 | |
| WO | WO2010/005482 A1 | 1/2010 | |
| WO | WO2010/067360 A2 | 6/2010 | |
| WO | WO2010/118035 A2 | 10/2010 | |
| WO | WO2013/044207 A1 | 3/2013 | |
| WO | WO2015/009907 A1 | 1/2015 | |
| WO | WO2016/134197 A1 | 8/2016 | |
| WO | WO2019/204884 A1 | 10/2019 | |
| WO | WO2023/141609 A1 | 7/2023 | |
| WO | WO2024/108110 A2 | 5/2024 | |

OTHER PUBLICATIONS

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Anderson et al.; Reflex principles of immunological homeostasis; Annu. Rev. Immunol.; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

Bernik et al., Vagus nerve stimulation attenuates cardiac TNF production in endotoxic shock, (supplemental to Shock, vol. 15, 2001, Injury, inflammation and sepsis: laboratory and clinical approaches, Shock, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression IN shock, New York Surgical Society, New York, NY, Apr. 11, 2001.

Bernik, et al., Pharmacological stimulation of the cholinergic anti-inflammatory pathway, The Journal of Experimental Medicine, vol. 195, No. 6, pp. 781-788, Mar. 18, 2002.

Besedovsky, H., et al., Immunoregulatory feedback between interleukin-1 and glucocorticoid hormones, Science, vol. 233, No. 4764, pp. 652-654, Aug. 1986.

Bhattacharya, S.K. et al., Central muscarinic receptor subtypes and carrageenin-induced paw oedema in rats, Res. Esp. Med. vol. 191(1), pp. 65-76, Dec. 1991.

Bianchi et al., Suppression of proinflammatory cytokines in monocytes by a tetravalent guanylhydrazone, Journal of Experimental Medicine, vol. 183, pp. 927-936, Mar. 1996.

Biggio et al.; Chronic vagus nerve stimulation induces neuronal plasticity in the rat hippocampus; Int. J. Neurpsychopharmacol.; vol. 12; No. 9; pp. 1209-1221; Oct. 2009.

Blackwell, T. S. et al., Sepsis and cytokines: current status, Br. J. Anaesth., vol. 77(1), pp. 110-117, Jul. 1996.

Blum, A. et al., Role of cytokines in heart failure, Am. Heart J., vol. 135(2), pp. 181-186, Feb. 1998.

Boldyreff, Gastric and intestinal mucus, its properties and physiological importance, Acta Medica Scandinavica (journal), vol. 89, Issue 1-2, pp. 1-14, Jan./Dec. 1936.

Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.

Borovikova et al., Efferent vagus nerve activity attenuates cytokine-mediated inflammation, Society for Neuroscience Abstracts, vol. 26, No. 102, Nov. 4-9, 2000 (abstract only).

Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.

Borovikova et al., Role of the efferent vagus nerve signaling in the regulation of the innate immune response to LPS, (supplemental to Shock, vol. 13, 2000, Molecular, cellular, and systemic pathobiological aspects and therapeutic approaches, abstracts, 5th World Congress on Trauma, Shock inflammation and sepsis—pathophysiology, immune consequences and therapy, Feb. 29, 2000-Mar. 4, 2000, Munich, DE), Abstract No. 166.

Borovikova et al., Role of the vagus nerve in the anti-inflammatory effects of CNI-1493, the FASEB journal, vol. 14, no. 4, 2000 (Experimental Biology 2000, San Diego, CA, Apr. 15-18, 2000, Abstract No. 97.9).

Borovikova et al., Vagotomy blocks the protective effects of I.C.V. CNI-1493 against LPS-induced shock, (Supplemental to Shock, vol. 11, 1999, Molecular, cellular, and systemic pathobioloigal aspects and therapeutic approaches, abstacts and program, Fourth international Shock Congress and 22nd Annual Conference on Shock, Philadelphia, PA, Jun. 12-16, 1999), Abstract No. 277.

Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.

Borovikova, L. V., et al., Vagus nerve stimulation attenuates the systemic inflammatory response to endotoxin, Nature, vol. 405, No. 6785: pp. 458-462, May 25, 2000.

Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.

Bulloch et al.; Characterization of choline O-acetyltransferase (ChAT) in the BALB/C mouse spleen; Int.J.Neurosci.; 76(1-2); pp. 141-149; May 1994.

Bumgardner, G. L. et al., Transplantation and cytokines, Seminars in Liver Disease, vol. 19, No. 2, Thieme Medical Publishers; pp. 189-204, ©1999.

(56) References Cited

OTHER PUBLICATIONS

Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.

Bushby et al; Centiles for adult head circumference; Archives of Disease in Childhood; vol. 67(10); pp. 1286-1287; Oct. 1992.

Cano et al.; Characterization of the central nervous system innervation of the rat spleen using viral transneuronal tracing; J.Comp Neurol.; 439(1); pp. 1-18; Oct. 2001.

Caravaca et al.; A novel flexible cuff-like microelectrode for dual purpose, acute and chronic electrical interfacing with the mouse cervical vagus nerve; Journal of Neural Engineering; 14(6);066005; Nov. 1, 2017.

Caravaca et al.; Vagus nerve stimulation reduces indoethacin-induced small bowel inflammation; Frontiers in Neuroscience; 15; Article 730407; doi10.3389/fnins.2021.730407; 9 pages; ; Jan. 2022.

Carteron, N. L., Cytokines in rheumatoid arthritis: trials and tribulations, Mol. Med. Today, vol. 6(8), pp. 315-323, Aug. 2000.

Cavaillon et al.; The pro-inflammatory cytokine casade; Immune Response in the Critically Ill; Springer-Verlag Berlin Hiedelberg; pp. 37-66; Jan. 21, 2002.

Chang et al.; Intermittent KHz-frequency electrical stimulation selectively engages small unmyelinated vagal afferents; bioRxiv; doi:10.1101/2021.01.30.428827. PPR:PPR276363; Feb. 1, 2021.

Chang et al.; Quantitative estimation of nerve fiber engagement by vagus nerve stimulation using physiological markers; Brain stimulation; 13(6); pp. 1617-1630; Sep. 18, 2020.

Cheyuo et al.; The parasympathetic nervous system in the quest for stroke therapeutics; J. Cereb. Blood Flow Metab.; 31(5); pp. 1187-1195; May 2011.

Choi et al.; Association of first, second, and third-line bDMARDs and tsDMARD with drug survival among seropositive rheumatoid arthritis patients: cohort study in a real world setting; Seminars in Arthritis and Rheumatism; 51(4); pp. 685-691; Aug. 2021.

Cicala et al., "Linkage between inflammation and coagulation: An update on the molecular basis of the crosstalk," Life Sciences, vol. 62(20); pp. 1817-1824, Apr. 1998.

Clark et al.; Enhanced recognition memory following vagus nerve stimulation in human subjects; Nat. Neurosci.; 2(1); pp. 94-98; Jan. 1999.

Cohen, "The immunopathogenesis of sepsis," Nature., vol. 420(6917): pp. 885-891, Dec. 2002.

Corcoran, et al., The effects of vagus nerve stimulation on pro- and anti-inflammatory cytokines in humans: a preliminary report, NeuroimmunoModulation, vol. 12(5), pp. 307-309, Sep. 2005.

Crusz et al.; Inflammation and cancer; advances and new agents; Nature reviews Clinical Oncology; 12(10); pp. 584-596; doi: 10.1038/nrclinonc.2015.105; Jun. 30, 2015.

Dake; Chronic cerebrospinal venous insufficiency and multiple sclerosis: Hostory and background; Techniques Vasc. Intervent. Radiol.; 15(2); pp. 94-100; Jun. 2012.

DAS, Critical advances in spticemia and septic shock, Critical Care, vol. 4, pp. 290-296, Sep. 7, 2000.

De Jonge et al.; Stimulation of the vagus nerve attenuates macrophage activation by activating the Jak2-STAT3 signaling pathway; Nature Immunnology; 6(8); pp. 844-851; Aug. 2005.

Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.

Diamond et al.; Mapping the immunological homunculus; Proc. Natl. Acad. Sci. USA; 108(9); pp. 3461-3462; Mar. 1, 2011.

Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.

Dinarello, C. A., The interleukin-1 family: 10 years of discovery, FASEB J., vol. 8, No. 15, pp. 1314-1325, Dec. 1994.

Dorr et al.; Effect of vagus nerve stimulation on serotonergic and noradrenergic transmission; J. Pharmacol. Exp. Ther.; 318(2); pp. 890-898; Aug. 2006.

Doshi et al., Evolving role of tissue factor and its pathway inhibitor, Crit. Care Med., vol. 30, suppl. 5, pp. S241-S250, May 2002.

Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.

Ellington et al., In vitro selection of RNA molecules that bind specific ligands, Nature, vol. 346, pp. 818-822, Aug. 30, 1990.

Ellrich et al.; Transcutaneous vagus nerve stimulation; Eur. Neurological Rev.; 6(4); pp. 254-256; Winter 2011.

Emery et al.; Rituximab versus an alternative TNF inhibitor in patients with rheumatoid arthritis who failed to respond to a single previous TNF inhibitor: switch-ra, a global, oberservational, comparative effectiveness study; Annals of the Rheumatic Diseases; 4(6); pp. 979-984; Jun. 2015.

Engineer et al.; Directing neural plasticity to understand and treat tinnitus; Hear. Res.; 295; pp. 58-66; Jan. 2013.

Engineer et al.; Reversing pathological neural activity using targeted plasticity; Nature; 470(7332); pp. 101-104; Feb. 3, 2011 (Author Manuscript).

Esmon, The protein C pathway, Crit. Care Med., vol. 28, suppl. 9, pp. S44-S48, Sep. 2000.

Fields; New culprits in chronic pain; Scientific American; pp. 50-57; Nov. 2009.

Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.

Fox, D. A., Cytokine blockade as a new strategy to treat rheumatoid arthritis, Arch. Intern. Med., vol. 160, pp. 437-444, Feb. 28, 2000.

Fox, et al., Use of muscarinic agonists in the treatment of Sjorgren' syndrome, Clin. Immunol., vol. 101, No. 3; pp. 249-263, Dec. 2001.

Fujii et al.; Simvastatin regulates non-neuronal cholinergic activity in T lymphocytes via CD11a-mediated pathways; J. Neuroimmunol.; 179(1-2); pp. 101-107; Oct. 2006.

Gao et al.; Investigation of specificity of auricular acupuncture points in regulation of autonomic function in anesthetized rats; Autonomic Neurosc.; 138(1-2); pp. 50-56; Feb. 29, 2008.

Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.

Gautron et al.; Neurobiology of inflammation-associated anorexia; Frontiers in Neuroscience; 3(59); 10 pages; Jan. 8, 2010.

Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.

Genovese et al.; Safety and efficacy of neurostimulation with a miniaturised vagus nerve stimulation device in patients with multidrug-refractory rheumatoid arthritis: a two-stage multicentre, randomised pilot study; The Lancet Rheumatology: 2(09); pp. e527-e538; Sep. 2020.

Ghelardini et al., S-(-)-ET 126: A potent and selective M1 antagonist in vitro and in vivo, Life Sciences, vol. 58, No. 12, pp. 991-1000, Feb. 1996.

Ghia, et al., The vagus nerve: a tonic inhibitory influence associated with inflammatory bowel disease in a murine model, Gastroenterology, vol. 131, No. 4, pp. 1122-1130, Oct. 2006.

Giebelen, et al., Stimulation of ?7 cholinergic receptors inhibits lipopolysaccharide-induced neutrophil recruitment by a tumor necrosis factor ?-independent mechanism, Shock, vol. 27, No. 4, pp. 443-447, Apr. 2007.

Gottenberg et al.; Non-TNF-targeted biologic vs a second anti-TNF drug to treat theumatoid arthritis in patients with insufficient response to a first anti TNF drug: a randomized clinical trial; JAMA; 316(11); pp. 1172-1180; Sep. 2016.

Goyal et al., Nature of the vagal inhibitory innervation to the lower esophageal sphincter, Journal of Clinical Investigation, vol. 55, pp. 1119-1126, May 1975.

(56)          References Cited

OTHER PUBLICATIONS

Gracie, J. A., et al., A proinflammatory role for IL-18 in rheumatoid arthritis, J. Clin. Invest., vol. 104, No. 10, pp. 1393-1401, Nov. 1999.

Granert et al., Suppression of macrophage activation with CNI-1493 increases survival in infant rats with systemic haemophilus influenzae infection, Infection and Immunity, vol. 68, No. 9, pp. 5329-5334, Sep. 2000.

Green et al., Feedback technique for deep relaxation, Psycophysiology, vol. 6, No. 3, pp. 371-377, Nov. 1969.

Gregory et al., Neutrophil-kupffer-cell interaction in host defenses to systemic infections, Immunology Today, vol. 19, No. 11, pp. 507-510, Nov. 1998.

Groves et al.; Recordings from the rat locus coeruleus during acute vagal nerve stimulation in the anaesthetised rat; Neuroscience Letters; 379(3); pp. 174-179; May 13, 2005.

Guarente, Leonard, Ph. D.; Sirtuins, Aging, and Medicine; N Engl J Med ; vol. 364:pp. 2235-2244; Jun. 2011.

Guslandi, M., Nicotine treatment for ulcerative colitis, Br. J. Clin. Pharmacol., vol. 48(4), pp. 481-484, Oct. 1999.

Hansson, E.; Could chronic pain and spread of pain sensation be induced and maintained by glial activation?. Acta Physiologica, vol. 187, Issue 1-2; pp. 321R327, May/Jun. 2006.

Harrison's Principles of Internal Medicine, 13th Ed., pp. 511-515 and 1433-1435, Mar. 1994.

Hatton et al.; Vagal nerve stimulation: overview and implications for anesthesiologists; Int'l Anesthesia Research Society; vol. 103; No. 5; pp. 1241-1249; Nov. 2006.

Hebb et al.; Creating the Feedback Loop: Closed-Loop Neurostimulation; Neurosurgery Clinics of North America; 25(1); pp. 187-204; Jan. 28, 2014.

Hirano, T., Cytokine suppresive agent improves survival rate in rats with acute pancreatitis of closed duodenal loop, J. Surg. Res., vol. 81, No. 2, pp. 224-229, Feb. 1999.

Hirao et al., The limits of specificity: an experimental analysis with RNA aptamers to MS2 coat protein variants, Mol. Divers., vol. 4, No. 2, pp. 75-89, 1999 (Accepted Jan. 13, 1999).

Hoffer et al.; Implantable electrical and mechanical interfaces with nerve and muscle; Annals of Biomedical Engineering; vol. 8; pp. 351-360; Jul. 1980.

Holladay et al., Neuronal nicotinic acetylcholine receptors as targets for drug discovery, Journal of Medicinal Chemistry, 40(26), pp. 4169-4194, Dec. 1997.

Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.

Housley et al.; Biomarkers in multiple sclerosis; Clinical Immunology; 161 (1); pp. 51-58; Nov. 2015.

Hsu, et al., Analysis of efficiency of magnetic stimulation, IEEE Trans. Biomed. Eng., vol. 50(11), pp. 1276-1285, Nov. 2003.

Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.

Hu, et al., The effect of norepinephrine on endotoxin-mediated macrophage activation, J. Neuroimmunol., vol. 31(1), pp. 35-42, Jan. 1991.

Huston et al.; Splenectomy inactivates the cholinergic antiinflammatory pathway during lethal endotoxemia and polymicrobial sepsis; J. Exp. Med. 2006; vol. 203, No. 7; pp. 1623-1628; Jun. 19, 2006.

Huston et al.; Transcutaneous vagus nerve stimulation reduces serum high mobility group box 1 levels and improves survival in murine sepsis; Crit. Care Med.; 35(12); pp. 2762-2768; Dec. 2007.

Hutchinson et al.; Proinflammatory cytokines oppose opioid induced acute and chronic analgesia; Brain Behav Immun.; vol. 22; No. 8; pp. 1178-1189; Nov. 2008.

Ilton et al., "Differential expression of neutrophil adhesion molecules during coronary artery surgery with cardiopulmonary bypass"

Journal of Thoracic and Cardiovascular Surgery, Mosby—Year Book, inc., St. Louis, Mo, US, pp. 930-937, Nov. 1, 1999.

Jacob et al., Detrimental role of granulocyte-colony stimulating factor in neuromyelitis optica: clinical case and histological evidence; Multiple Sclerosis Journal; 18(12); pp. 1801-1803; Dec. 2012.

Jaeger et al., The structure of HIV-1 reverse transcriptase complexed with an RNA pseudoknot inhibitor, The EMBO Journal, 17(15), pp. 4535-4542, Aug. 1998.

Jander, S. et al., Interleukin-18 is induced in acute inflammatory demyelinating polymeuropathy, J. Neuroimmunol., vol. 114, pp. 253-258, Mar. 2001.

Joshi et al., Potent inhibition of human immunodeficiency virus type 1 replection by template analog reverse transcriptase , J. Virol., 76(13), pp. 6545-6557, Jul. 2002.

Kalishevskaya et al. "The character of vagotomy-and atropin-induced hypercoagulation," Sechenov Physiological Journal of the USSR, 65(3): pp. 398-404, Mar. 1979.

Kalishevskaya et al.; Nervous regulation of the fluid state of the blood; Usp. Fiziol. Nauk;, vol. 13; No. 2; pp. 93-122; Apr.-Jun. 1982.

Kanai, T. et al., Interleukin-18 and Crohn's disease, Digestion, vol. 63, suppl. 1, pp. 37-42; 2001 (year of pub. sufficiently earlier than effective US filing date and any foreign priority date).

Katagiri, M., et al., Increased cytokine production by gastric mucosa in patients with helicobacter pylori infection, J. Clin, Gastroenterol., vol. 25, Suppl. 1, pp. S211-S214, 1997.

Katsavos et al.; Biomarkers in multiple sclerosis: an up-to-date overview; Multiple Sclerosis International; vol. 2013, Article ID 340508, 20 pages; Jan. 1, 2013.

Kawahara et al.; SIRT6 links histone H3 lysine 9 deacetylation to NF-kappaB-dependent gene expression and organismal life span.; Cell. ; vol. 136; No. 1; pp. 62-74; Jan. 2009.

Kawashima, et al., Extraneuronal cholinergic system in lymphocytes, Pharmacology & Therapeutics, vol. 86, pp. 29-48, Apr. 2000.

Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Khatun, S., et al., "Induction of hypercoagulability condition by chronic localized cold stress in rabbits," Thromb. and Haemost., 81(3): pp. 449-455, Mar. 1999.

Kimball, et al., Levamisole causes differential cytokine expression by elicited mouse peritoneal macrophases, Journal of Leukocyte Biology, vol. 52, No. 3, pp. 349-356, Sep. 1992 (abstract only).

Kimmings, A. N., et al., Systemic inflammatory response in acute cholangitis and after subsequent treatment, Eur. J. Surg., vol. 166, pp. 700-705, Sep. 2000.

Kirchner et al.; Left vagus nerve stimulation suppresses experimentally induced pain; Neurology; vol. 55; pp. 1167-1171; Oct. 2000.

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.

Koopman et al.; Pilot study of stimulation of the cholinergic anti-inflammatory pathway with an implantable vagus nerve stimulation device in patients with rheumatoid arthritis; 2012 ACR/ARHP Annual Meeting; Abstract No. 451; 4 pages; retrieved from the internet (https:/acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.

Koopman et al.; THU0237 first-in-human study of vagus nerve stimulation for rheumatoid arthritis: clinical and biomarker results

(56)　　　　　References Cited

OTHER PUBLICATIONS through day 84; Annals of the Rheumatic Diseases; 72(Suppl 3):A245; Jun. 1, 2013 (Abstract Only).

Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.

Krarup et al; Conduction studies in peripheral cat nerve using implanted electrodes: I. methods and findings in controls; Muscle & Nerve; vol. 11; pp. 922-932; Sep. 1988.

Kudrjashov, et al. "Reflex nature of the physiological anticoagulating system," Nature, vol. 196(4855): pp. 647-649; Nov. 17, 1962.

Kumins, N. H., et al., Partial hepatectomy reduces the endotoxin-induced peak circulating level of tumor necrosis factor in rats, Shock, vol. 5, No. 5, pp. 385-388, May 1996.

Kuznik, "Role of the vascular wall in the process of hemostatis," Usp Sovrem Biol., vol. 75(1): pp. 61-85; 1973 (the year of publication is sufficiently earlier than the effective U.S. filing date and any foreign priority date so that the particular month of publication is not in issue).

Kuznik, et al., "Blood Coagulation in stimulation of the vagus nerve in cats," Biull. Eskp. Biol. Med., vol. 78(7): pp. 7-9; 1974 (the year of publication is sufficiently earlier than the effective U.S. filing date and any foreign priority date so that the particular month of publication is not in issue).

Kuznik, et al., "Heart as an efferent regulator of the process of blood coagulation and fibrinolysis," Kardiologiia, vol. 13 (3): pp. 10-17; 1973 (the year of publication is sufficiently earlier than the effective U.S. filing date and any foreign priority date so that the particular month of publication is not in issue).

Kuznik, et al., "Role of the heart and vessels in regulating blood coagulation and fibrinolysis," Kagdiologiia, vol. 13(4): pp. 145-154, Apr. 1973.

Kuznik, et al., "Secretion of blood coagulation factors into saliva under conditions of hypo-and hypercoagulation," Voprosy Meditsinskoi Khimil, vol. 19(1): pp. 54-57; 1973(the year of publication is sufficiently earlier than the effective U.S. filing date and any foreign priority date so that the particular month of publication is not in issue).

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.

Kuznik, et al., "The role of the vascular wall in the mechanism of control of blood coagulation and fibrinolysis on stimulation of the vagus nerve," Cor Vasa, vol. 17(2): pp. 151-158; 1975 (the year of publication is sufficiently earlier than the effective U.S. filing date and any foreign priority date so that the particular month of publication is not in issue).

Lang, et al., "Neurogienic control of cerebral blood flow," Experimental Neurology, 43(1): pp. 143-161, Apr. 1974.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.

LeNovere, N. et al., Molecular evolution of the nicotinic acetylcholine receptor: an example of multigene family in excitable cells, J. Mol. Evol., 40, pp. 155-172, Feb. 1995.

Leonard, S. et al., Neuronal nicotinic receptors: from structure to function, Nicotine & Tobacco Res. 3:203-223, Aug. 2001.

Lips et al.; Coexpression and spatial association of nicotinic acetylcholine receptor subunits alpha7 and alpha10 in rat sympathetic neurons; J.Mol. Neurosci.; 30; pp. 15-16; Feb. 2006.

Lipton, J. M. et al.; Anti-inflammatory actions of the neuroimmunomodulator ?-MSH, Immunol. Today, vol. 18, pp. 140-145, Mar. 1997.

Liu et al.; A neuroanatomical basis for electroacupuncture to drive the vagal-adrenal axis; Nature; 598(7882); pp. 641-645; 37 pages; (Author Manuscript); Oct. 2021.

Loeb et al.; Cuff electrodes for chronic stimulation and recording of peripheral nerve activity; Journal of Neuroscience Methods; vol. 64; pp. 95-103; Jan. 1996.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.

Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).

Martindale: The Extra Pharmacopoeia; 28th Ed. London; The Pharmaceutical Press; pp. 446-485; ©1982.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

Mayo Clinic; The factsheet of vagus nerve stimulation from the Mayo Clinic website: www.mayoclinic.org/tests-procedures/vagus-nerve-sti mulation/about/pac-20384565; retrieved from the internet on Sep. 28, 2021.

McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.

McLean et al.; Delayed nerve stimulation promotes axon-protective neurofilament phosphorylation, accelerates immune cell clearance and enhances remyelination in vivo in focally demyelinated nerves; PloS one; 9(10); e110174; 17 pages; Oct. 13, 2014.

Miguel-Hidalgo, J.J.; The role of glial cells in drug abuse; Current Drug Abuse Reviews; vol. 2; No. 1; pp. 76-82; Jan. 2009.

Milligan et al.; Pathological and protective roles of glia in chronic pain; Nat Rev Neurosci.; vol. 10; No. 1; pp. 23-26; Jan. 2009.

Minnich et al.; Anti-cytokine and anti-inflammatory therapies for the treatment of severe sepsis: progress and pitfalls; Proceedings of the Nutrition Society; vol. 63(3); pp. 437-441; Aug. 2004.

Mishchenko, et al., "Coagulation of the blood and fibrinolysos in dogs during vagal stimulation," Sechenov Physiological Journal of the USSR, vol. 61(1): pp. 101-107, 1975.

Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, 1974.

Molina et al., CNI-1493 attenuates hemodynamic and pro-inflammatory responses to LPS, Shock, vol. 10, No. 5, pp. 329-334, Nov. 1998.

Monaco et al.; Anti-TNF therapy:past,present, and future; International Immunology; 27(1); pp. 55-62; Jan. 2015.

Nadol et al., "Surgery of the Ear and Temporal Bone," Lippinkott Williams & Wilkins, 2nd Ed., 2005, (Publication date: Sep. 21, 2004), p. 580.

Nagashima et al., Thrombin-activatable fibrinolysis inhibitor (TAFI) deficiency is compatible with murine life, J. Clin. Invest., 109, pp. 101-110, Jan. 2002.

Nathan, C. F., Secretory products of macrophages, J. Clin. Invest., vol. 79(2), pp. 319-326, Feb. 1987.

Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.

Navzer et al.; Reversing pathological neural activity using targeted plasticity; Nature; 470(7332); pp. 101-104; Feb. 3, 2011.

Neuhaus et al.; P300 is enhanced in responders to vagus nerve stimulation for treatment of major depressive disorder; J. Affect. Disord.; 100(1-3); pp. 123-128; Jun. 2007.

Noguchi et al., Increases in Gastric acidity in response to electroacupuncture stimulation of hindlimb of anesthetized rats, Jpn. J. Physiol., 46(1), pp. 53-58, Feb. 1996.

Norton, Can ultrasound be used to stimulate nerve tissue, BioMedical Engineering OnLine, 2(1), pp. 6, Mar. 4, 2003.

Olofsson et al.; Rethinking inflammation: neural circuits in the regulation of immunity; Immunological Reviews; 248(1); pp. 188-204; Jul. 2012.

(56)  References Cited

OTHER PUBLICATIONS

Olofsson et al.; Single-pulse and unidirectional electrical activation of the cervical vagus nerve reduces tumor necrosis factor in endotoxemia; Bioelectronic Medicine; 2(1); pp. 37-42; Jun. 2015.

Oshinsky et al.; Non-invasive vagus nerve stimulation as treatment for trigeminal allodynia; Pain; 155(5); pp. 1037-1042; May 2014.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.

Palov et al.; The cholinergic anti-inflammatory pathway: a missing link in neuroimmunomodulation; Molecular Medicine; 9(5); pp. 125-134; May 2003.

Pasricha et al.; Sacral nerve stimulation prompts vagally-mediated amelioration of rodent colitis; Physiological Reports; 8(1); e14294; 7 pages; Jan. 2020.

Pateyuk, et al., "Treatment of Botkin's disease with heparin," Klin. Med., vol. 51(3): pp. 113-117, Mar. 1973.

Pavlov et al.; The cholinergic anti-inflammatory pathway; Brain, Behavior, and Immunity; 19; p. 493-499; Nov. 2005.

Pavlov et al; Controlling inflammation: the cholinergic anti-inflammatory pathway; Biochem. Soc. Trans.; 34(Pt 6); pp. 1037-1040; Dec. 2006.

Payne, J. B. et al., Nicotine effects on PGE2 and IL-1 beta release by LPS-treated human monocytes, J. Perio. Res., vol. 31, No. 2, pp. 99-104, Feb. 1996.

Peuker; The nerve supply of the human auricle; Clin. Anat.; 15(1); pp. 35-37; Jan. 2002.

Pongratz et al.; The sympathetic nervous response in inflammation; Arthritis Research and Therapy; 16(504); 12 pages; retrieved from the internet (http://arthritis-research.com/content/16/6/504) ; Jan. 2014.

Prystowsky, J. B. et al., Interleukin-1 mediates guinea pig gallbladder inflammation in vivo, J. Surg. Res., vol. 71, No. 2, pp. 123-126, Aug. 1997.

Pulkki, K. J., Cytokines and cardiomyocyte death, Ann. Med., vol. 29(4), pp. 339-343, Aug. 1997.

Pullan, R. D., et al., Transdermal nicotine for active ulceratiive colitis, N. Engl. J. Med., vol. 330, No. 12, pp. 811-815, Mar. 24, 1994.

Pulvirenti et al; Drug dependence as a disorder of neural plasticity:focus on dopamine and glutamate; Rev Neurosci.; vol. 12; No. 2; pp. 141-158; Apr./Jun. 2001.

Rahman et al.; Mammalian Sirt 1: Insights on its biological functions; Cell Communications and Signaling; vol. 9; No. 11; pp. 1-8; May 2011.

Rayner, S. A. et al., Local bioactive tumour necrosis factor (TNF) in corneal allotransplantation, Clin. Exp. Immunol., vol. 122, pp. 109-116, Oct. 2000.

Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.

Rendas-Baum et al.; Evaluating the efficacy of sequential biologic therapies for rheumatoid arthritis patients with an inadequate response to tumor necrosis factor-alpha inhibitors; Arthritis research and therapy; 13; R25; 15 pages; ; Feb. 2011.

Rinner et al.; Rat lymphocytes produce and secrete acetylcholine in dependence of differentiation and activation; J.Neuroimmunol.; 81(1-2); pp. 31-37; Jan. 1998.

Robinson et al.; Studies with the Electrocardiogram the Action of the Vagus Nerve on the Human Heart; J Exp Med; 14(3):217-234; Sep. 1911.

Romanovsky, A. A., et al., The vagus nerve in the thermoregulatory response to systemic inflammation, Am. J. Physiol., vol. 273, No. 1 (part 2), pp. R407-R413, Jul. 1, 1997.

Rosas-Ballina et al.; Acetylcholine-synthesizing T cells relay neural signals in a vagus nerve circuit Science; 334(6052); pp. 98-101; 10 pages; (Author Manuscript); Oct. 2011.

Saghizadeh et al.; The expression of TNF? by human muscle; J. Clin. Invest.; vol. 97; No. 4; pp. 1111-1116; Feb. 15, 1996.

Saindon et al.; Effect of cervical vagotomy on sympathetic nerve responses to peripheral interleukin-1beta; Auton.Neuroscience Basic and Clinical; 87; pp. 243-248; Mar. 23, 2001.

Saito, Involvement of muscarinic M1 receptor in the central pathway of the serotonin-induced bezold-jarisch reflex in rats, J. Autonomic Nervous System, vol. 49, pp. 61-68, Sep. 1994.

Sandborn, W. J., et al., Transdermal nicotine for mildly to moderately active ulcerative colitis, Ann. Intern. Med, vol. 126, No. 5, pp. 364-371, Mar. 1, 1997.

Sato, E., et al., Acetylcholine stimulates alveolar macrophages to release inflammatory cell chemotactic activity, Am. J. Physiol., vol. 274, pp. L970-L979, Jun. 1998.

Sato, K.Z., et al., Diversity of mRNA expression for muscarinic acetylcholine receptor subtypes and neuronal nicotinic acetylcholine receptor subunits in human mononuclear leukocytes and leukemic cell lines, Neuroscience Letters, vol. 266, pp. 17-20, Apr. 30, 1999.

Scheinman, R. I., et al., Role of transcriptional activation of I?B? in mediation of immunosuppression by glucocorticoids, Science, vol. 270, No. 5234, pp. 283-286, Oct. 13, 1995.

Schneider et al., High-affinity ssDNA inhibitors of the review transcriptase of type 1 human immunodeficiency virus, Biochemistry, 34(29), pp. 9599-9610, Jul. 1995.

Shafer, Genotypic testing for human immunodeficiency virus type 1 drug resistance, Clinical Microbiology Reviews, vol. 15, pp. 247-277, Apr. 2002.

Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.

Sher, M. E., et al., The influence of cigarette smoking on cytokine levels in patients with inflammatory bowel disease, Inflamm. Bowel Dis., vol. 5, No. 2, pp. 73-78, May 1999.

Shi et al.; Effects of efferent vagus nerve excitation on inflammatory response in heart tissue in rats with endotoxemia; vol. 15, No. 1; pp. 26-28; Jan. 2003 (Eng. Abstract).

Snyder et al., Correction of hemophilia B in canine and murine models using recombinant adeno-associated viral vectors; Nature Medicine, 5(1), pp. 64-70, Jan. 1999.

Sokratov, et al. "The role of choline and adrenegic structures in regulation of renal excretion of hemocoagulating compounds into the urine," Sechenov Physiological Journal of the USSR, vol. 63(12): pp. 1728-1732, 1977.

Stalcup et al., Endothelial cell functions in the hemodynamic responses to stress, Annals of the New York Academy of Sciences, vol. 401, pp. 117-131, Dec. 1982.

Steinlein, New functions for nicotine acetylcholine receptors?, Behavioural Brain Res., vol. 95(1), pp. 31-35, Sep. 1998.

Sternberg, E. M., Perspectives series: cytokines and the brain 'neural-immune interactions in health and disease,' J. Clin. Invest., vol. 100, No. 22, pp. 2641-2647, Dec. 1997.

Stevens et al.; The anti-inflammatory effect of some immunosuppressive agents; J. Path.; 97(2); pp. 367-373; Feb. 1969.

Strojnik et al.; Treatment of drop foot using and implantable peroneal underknee stimulator; Scand. J. Rehab. Med.; vol. 19(1); pp. 37R43; Dec. 1986.

Strowig et al.; Inflammasomes in health and disease; Nature; vol. 481; pp. 278-286; doi: 10.1038/nature10759; Jan. 19, 2012.

Sugano et al., Nicotine inhibits the production of inflammatory mediators in U937 cells through modulation of nuclear factor-kappaß activation, Biochemical and Biophysical Research Communications, vol. 252, No. 1, pp. 25-28, Nov. 9, 1998.

Suter et al.; Do glial cells control pain?; Neuron Glia Biol.; vol. 3; No. 3; pp. 255-268; Aug. 2007.

Swick et al.; Locus coeruleus neuronal activity in awake monkeys: relationship to auditory P300-like potentials and spontaneous EEG. Exp. Brain Res.; 101(1); pp. 86-92; Sep. 1994.

Sykes, et al., An investigation into the effect and mechanisms of action of nicotine in inflammatory bowel disease, Inflamm. Res., vol. 49, pp. 311-319, Jul. 2000.

(56)          References Cited

OTHER PUBLICATIONS

Takeuchi et al., A comparison between chinese blended medicine "Shoseiryuto" tranilast and ketotifen on the anit-allergic action in the guinea pigs, Allergy, vol. 34, No. 6, pp. 387-393, Jun. 1985 (eng. abstract).

Tekdemir et al.; A clinico-anatomic study of the auricular branch of the vagus nerve and amold's ear-cough reflex; Surg. Radiol. Anat.; 20(4); pp. 253-257; Mar. 1998.

Toyabe, et al., Identification of nicotinic acetylcholine receptors on lymphocytes in the periphery as well as thymus in mice, Immunology, vol. 92(2), pp. 201-205, Oct. 1997.

Tracey et al., Mind over immunity, Faseb Journal, vol. 15, No. 9, pp. 1575-1576, Jul. 2001.

Tracey, K. J. et al., Anti-cachectin/TNF monoclonal antibodies prevent septic shock during lethal bacteraemia; Nature, 330: pp. 662-664, Dec. 23, 1987.

Tracey, K. J. et al., Physiology and immunology of the cholinergic antiinflammatory pathway; J Clin Invest.; vol. 117: No. 2; pp. 289-296; Feb. 2007.

Tracey, K. J. et al., Shock and tissue injury induced by recombinant human cachectin, Science, vol. 234, pp. 470-474, Oct. 24, 1986.

Tracey, K. J.; Reflex control of immunity; Nat Rev Immunol; 9(6); pp. 418-428; Jun. 2009.

Tracey, K.J., The inflammatory reflex, Nature, vol. 420, pp. 853-859, Dec. 19-26, 2002.

Tsutsui, H., et al., Pathophysiologiemmatory liver diseases; Immunol. Rev., 174:192-209, Apr. 2000.

Tuerk et al., RNA pseudoknots that inhibit human immunodeficiency virus type 1 reverse transcriptase; Proc. Natl. Acad. Sci. USA, 89, pp. 6988-6992, Aug. 1992.

Tuerk et al., Systematic evolution of ligands by exponential enrichment: RNA ligands to bacteriophage T4 DNA polymerase; Science, 249(4968), pp. 505-510, Aug. 3, 1990.

Van Der Horst et al.; Stressing the role of FoxO proteins in lifespan and disease; Nat Rev Mol Cell Biol.; vol. 8; No. 6; pp. 440-450; Jun. 2007.

Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.

Vanhoutte, et al., Muscarinic and beta-adrenergic prejunctional modulation of adrenergic neurotransmission in the blood vessel wall, Gen Pharmac., vol. 14(1), pp. 35-37, Jan. 1983.

VanWesterloo, et al., The cholinergic anti-inflammatory pathway regulates the host response during septic peritonitis, The Journal of Infectious Diseases, vol. 191, pp. 2138-2148, Jun. 15, 2005.

Ventureyra, Transcutaneous vagus nerve stimulation for partial onset seizure therapy, Child's Nerv Syst, vol. 16(2), pp. 101-102, Feb. 2000.

Vida et al.; Aplha 7-cholinergic receptor mediates vagal induction of splenic norepinephrine; Journal of Immunology; 186(7); pp. 4340-4346; 16 pages; (Author Manuscript); Apr. 2011.

Vijayaraghavan, S.; Glial-neuronal interactions-implications for plasticity anddrug addictionl AAPS J.; vol. 11; No. 1; pp. 123-132; Mar. 2009.

Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.

Von Känel, et al., Effects of non-specific ?-adrenergic stimulation and blockade on blood coagulation in hypertension, J. Appl. Physiol., vol. 94, pp. 1455-1459, Apr. 2003.

Von Känel, et al., Effects of sympathetic activation by adrenergic infusions on hemostasis in vivo, Eur. J. Haematol., vol. 65: pp. 357-369, Dec. 2000.

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.

Wang et al; Nicotinic acetylcholine receptor alpha7 subunit is an essential regulator of inflammation; Nature; 421; 384-388; Jan. 23, 2003.

Wang, H., et al., HMG-1 as a late mediator of endotoxin lethality in mice, Science, vol. 285, pp. 248-251, Jul. 9, 1999.

Waseman, S. et al., TNF-? dysregulation in asthma: relationship to ongoing corticosteroid therapy, Can. Respir. J., vol. 7, No. 3, pp. 229-237, May-Jun. 2000.

Watanabe, H. et al., The significance of tumor necrosis factor (TNF) levels for rejection of joint allograft, J. Reconstr. Microsurg., vol. 13, No. 3, pp. 193-197, Apr. 1997.

Wathey, J.C. et al., Numerical reconstruction of the quantal event at nicotinic synapses; Biophys. J., vol. 27: pp. 145-164, Jul. 1979.

Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.

Watkins, L.R. et al., Implications of immune-to-brain communication for sickness and pain, Proc. Natl. Acad. Sci. U.S.A., vol. 96(14), pp. 7710-7713, Jul. 6, 1999.

Webster's Dictionary, definition of "intrathecal", online version accessed Apr. 21, 2009.

Weiner, et al., "Inflammation and therapeutic vaccination in CNS diseases," Nature., vol. 420(6917): pp. 879-884, Dec. 19-26, 2002.

Westerheide et al.; Stress-inducible regulation of heat shock factor 1 by the deacetylase SIRT1.; Science; vol. 323; No. 5717; pp. 1063-1066; Feb. 2009.

Whaley, K. et al., C2 synthesis by human monocytes is modulated by a nicotinic cholinergic receptor, Nature, vol. 293, pp. 580-582, Oct. 15, 1981.

Woiciechowsky, C. et al., Sympathetic activation triggers systemic interleukin-10 release in immunodepression induced by brain injury, Nature Med., vol. 4, No. 7, pp. 808-813, Jul. 1998.

Yang et al.; Acetylcholine inhibits LPS-induced MMP-9 production and ccell migration via the alpha7 nAChR-JAK2/STAT3 pathway in RAW264.7 cells; Cellular Physiology and Biochemistry; 36(5); pp. 2025-2038; (the year of publication is sufficiently earlier than the effective U.S. filing date and any foreign priority date so that the particular month of publication is not in issue) 2015.

Yang et al.; Axon myelination and electrical stimulation in a microfluidic, compartmentalized cell culture platform; Neuromolecular medicine; vol. 14; pp. 112-118; Jun. 2012.

Yeh, S.S. et al., Geriatric cachexia: the role of cytokines, Am. J. Clin. Nutr., vol. 70(2), pp. 183-197, Aug. 1999.

Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.

Zamotrinsky et al.; Vagal neurostimulation in patients with coronary artery disease; Auton. Neurosci.; 88(1-2); pp. 109-116; Apr. 2001.

Zhang et al., Tumor necrosis factor, The Cytokine Handbook, 3rd ed., Ed. Thompson, Academic Press, pp. 517-548, Jul. 1, 1998.

Zhang et al.; Chronic vagus nerve stimulation improves autonomic control and attenuates systemic inflammation and heart failure progression in a canine high-rate pacing model; Circulation Heart Fall., 2; pp. 692-699; Nov. 2009.

Zhang et al.; Roles of SIRT1 in the acute and restorative phases following induction of inflammation.; J Biol Chem.; vol. 285; No. 53; pp. 41391-401; Dec. 2010.

Zhao et al.; Transcutaneous auricular vagus stimulation protects endotoxemic rat from lipopolysaccharide-induced inflammation; Evid. Based Complement Alternat. Med., vol. 2012; Article ID 627023; 10 pages; Dec. 29, 2012.

Zitnik et al.; Treatment of chronic inflammatory diseases with implantable medical devices; Cleveland Clinic Journal of Medicine; 78(Suppl 1); pp. S30-S34; Aug. 2011.

Levine et al.; U.S. Appl. No. 18/730,753 entitled "Treatment of inflammatory disorders," filed Jul. 19, 2024.

Levine et al.; U.S. Appl. No. 18/893,907 entitled "Control of vagal stimulation," filed Sep. 23, 2024.

Migliore et al.; Cycling of tumor necrosis factor inhibitors versus switching to different mechanism of action therapy in rheumatoid arthritis patients with inadequate response to tumor necrosis factor inhibitors: a bayesian network meta-analysis; Therapeutic Advances in Musculoskeletal Disease; vol. 13; DOI 10.1177/1759720X211002682; 14 pages; Mar. 2021.

(56) References Cited

OTHER PUBLICATIONS

Pianca et al.; Endurance training induces structural and morphoquantitative changes in rat vagus nerve; Brazilian Journal of Sports Medicine; 21(5); pp. 403-406; 2015.

Faltys et al.; U.S. Appl. No. 19/028,434 entitled "Neural stimulation devices and systems for treatment of chronic inflammation," filed Jan. 17, 2025.

Levine et al.; U.S. Appl. No. 19/235,529 entitled "Extremely low duty-cycle activation of the cholinergic anti-inflammatory pathway to treat chronic inflammation," filed Jun. 11, 2025.

Datta-Chaudhuri et al.; U.S. Appl. No. 19/130,899 entitled "Systems and methods for closed-loop neuromodulation using multiple biological signals," filed May 16, 2025.

Cui et al.; Response of human oligodendrocyte progenitors to growth factors and axon signals; Journal of Neuropathology & Experimental Neurology; 69(9); pp. 930-944; Sep. 1, 2010.

Lv et al.; The role of the cholinergic anti?inflammatory pathway in autoimmune rheumatic diseases; Scandinavian Journal of Immunology; 94(4); e13092; 12 pages; Oct. 2021.

Shon et al.; Fully implantable plantar cutaneous augmentation system for rats using closed-loop electrical nerve stimulation; IEEE transactions on biomedical circuits and systems; 15(2); pp. 326-338; Apr. 16, 2021.

Wright et al.; A fully implantable wireless bidirectional neuromodulation system for mice; Biosensors and Bioelectronics; vol. 200; 113886; Mar. 15, 2022.

* cited by examiner

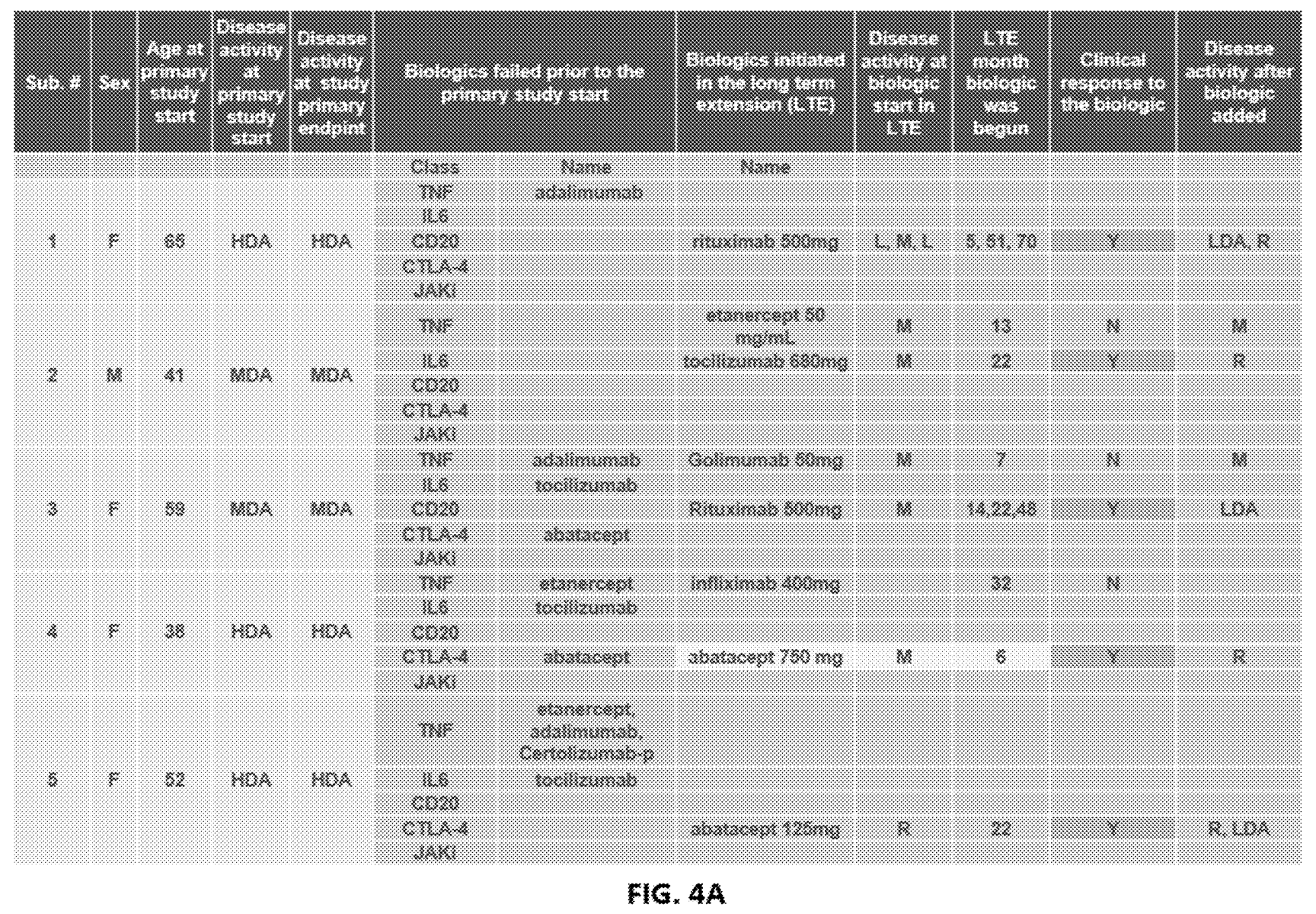

| Sub # | Sex | Age at primary study start | Disease activity at primary study start | Disease activity at study primary endpoint | Biologics failed prior to the primary study start — Class | Name | Biologics initiated in the long term extension (LTE) — Name | Disease activity at biologic start in LTE | LTE month biologic was begun | Clinical response to the biologic | Disease activity after biologic added |
|---|---|---|---|---|---|---|---|---|---|---|---|
| 1 | F | 65 | HDA | HDA | TNF | adalimumab | rituximab 500mg | L,M,L | 3,51,70 | Y | LDA,R |
|  |  |  |  |  | IL6 |  |  |  |  |  |  |
|  |  |  |  |  | CD20 |  |  |  |  |  |  |
|  |  |  |  |  | CTLA-4 |  |  |  |  |  |  |
|  |  |  |  |  | JAK1 |  |  |  |  |  |  |
| 2 | M | 41 | MDA | MDA | TNF | etanercept 50 mg/ml | | M | 13 | N | M |
|  |  |  |  |  | IL6 | tocilizumab 600mg | | M | 22 | Y | R |
|  |  |  |  |  | CD20 |  |  |  |  |  |  |
|  |  |  |  |  | CTLA-4 |  |  |  |  |  |  |
|  |  |  |  |  | JAK1 |  |  |  |  |  |  |
| 3 | F | 59 | MDA | MDA | TNF | adalimumab | Golimumab 50mg | M | 7 | N | M |
|  |  |  |  |  | IL6 | tocilizumab |  |  |  |  |  |
|  |  |  |  |  | CD20 |  |  |  |  |  |  |
|  |  |  |  |  | CTLA-4 | abatacept |  |  |  |  |  |
|  |  |  |  |  | JAK1 |  |  |  |  |  |  |
| 4 | F | 38 | HDA | HDA | TNF | etanercept | Rituximab 500mg | M | 14,22,45 | Y | LDA |
|  |  |  |  |  | IL6 | tocilizumab | infliximab 400mg | M | 32 | N |  |
|  |  |  |  |  | CD20 |  | abatacept 750 mg | M | 6 | Y | R |
|  |  |  |  |  | CTLA-4 |  |  |  |  |  |  |
|  |  |  |  |  | JAK1 |  |  |  |  |  |  |
| 5 | F | 52 | HDA | HDA | TNF | etanercept, adalimumab, Certolizumab-p | abatacept 125mg | R | 22 | Y | R,LDA |
|  |  |  |  |  | IL6 | tocilizumab |  |  |  |  |  |
|  |  |  |  |  | CD20 |  |  |  |  |  |  |
|  |  |  |  |  | CTLA-4 |  |  |  |  |  |  |
|  |  |  |  |  | JAK1 |  |  |  |  |  |  |

FIG. 4A

| Sub # | Sex | Age at primary study start | Disease activity at primary study start | Disease activity at primary study endpoint | Biologics failed prior to the primary study start | Biologics initiated in the long term extension (LTE) | Disease activity at biologic start in LTE | LTE month biologic was begun | Clinical response to the biologic | Disease activity after biologic added |
|---|---|---|---|---|---|---|---|---|---|---|
| 6 | F | 44 | HDA | MDA | TNF: infliximab etanercept; IL6 | tocilizumab 162mg/mL | H | 25 | Y | MDA, then H |
| 7 | F | 46 | HDA | LDA | CD20; CTLA-4; JAK1: Rituximab Abatacept; TNF: infliximab etanercept adalimumab; IL6: tocilizumab | adalimumab 50mg/mL; tocilizumab 400mg | H; M | 4; 6 | Y; Y | MDA; LDA |
| 8 | F | 37 | HDA | LDA | TNF: infliximab etanercept adalimumab; IL6; CD20; CTLA-4; JAK1: abatacept | tocilizumab 162mg; Rituximab 500mg | M; H | 12; 19 | N; Y | H; R* |
| 9 | F | 41 | HDA | HDA | TNF: adalimumab Certolizumab; IL6; CD20; CTLA-4; JAK1: abatacept | Rituximab 500mg | H, M | 8, 22, 34, 48 | Y | R |

R* refers to long term remission after 1 dose
R refers to into LDA then remission

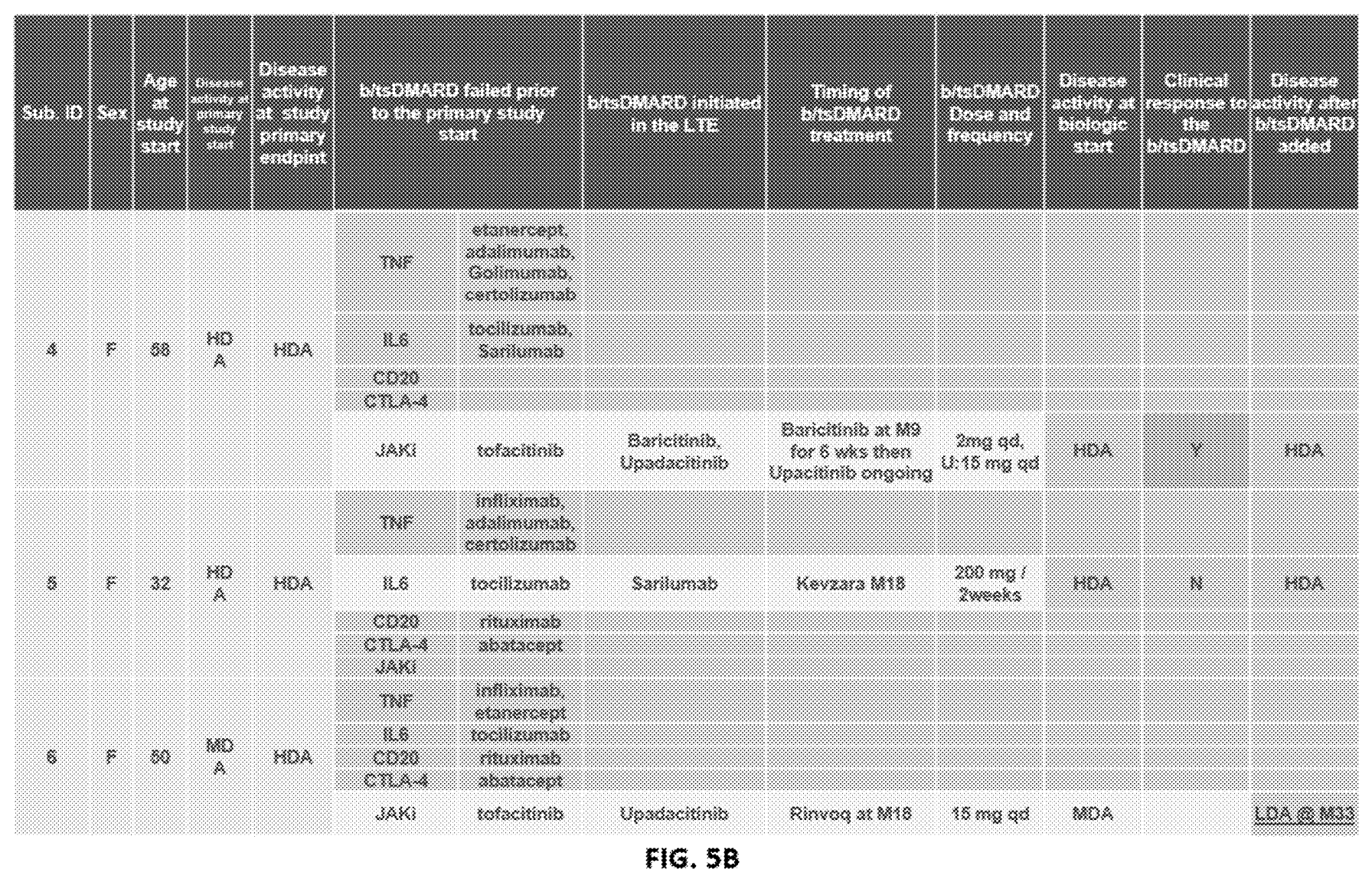

| Sub ID | Sex | Age at study start | Disease activity prior to primary study | bDMARD failed prior to primary study (reason for failure) | bDMARD initiated in the LTE | Timing of bDMARD treatment | bitsDMARD Dose prior to therapy | Disease activity at study of change | Clinical response to DMARD | Disease activity DMARD |
|---|---|---|---|---|---|---|---|---|---|---|
| 4 | F | 58 | HDA | TNF: etanercept, adalimumab, golimumab, certolizumab; IL6: tocilizumab, sarilumab; CD20; CTLA-4; JAK1: tofacitinib | Baricitinib, Upadacitinib | Baricitinib at M9 for 6 wks then Upadacitinib ongoing | 2mg qd, 0.15 mg qd | HDA | Y | HDA |
| 5 | F | 32 | HDA | TNF: infliximab, adalimumab, certolizumab; IL6: tocilizumab; CD20; CTLA-4; JAK1 | Sarilumab | Kevzara M18 | 200 mg / 2weeks | HDA | N | HDA |
| 6 | F | 58 | HDA | TNF: infliximab, etanercept; IL6: tocilizumab, rituximab, abatacept; CD20; CTLA-4; JAK1: tofacitinib | Upadacitinib | Rinvoq at M18 | 15 mg qd | MDA | | LDA @ M30 |

FIG. 5B

| Sub ID | Sex | Age at study start | Disease activity at study start | Disease activity at study primary endpoint | btsDMARD failed prior to the primary study start | btsDMARD initiated in the LTE | Timing of btsDMARD treatment | btsDMARD Dose and frequency | Disease activity at biologic initiation start | Clinical response to btsDMARD | Disease activity after btsDMARD |
|---|---|---|---|---|---|---|---|---|---|---|---|
| 7 | F | 66 | HDA | LDA | TNF: etanercept, certolizumab; IL6: tocilizumab; CD20; CTLA4 | | | | | | |
| | | | | | JAKi: abatacept | Upadacitinib | Rinvoq M24 to ongoing | 15 mg qd | Remission | Y | R.LDA |
| 8 | F | 53 | HDA | LDA | TNF: adalimumab; IL6: tocilizumab; CD20; CTLA4 | | | | | | |
| | | | | | JAKi: Tofacitinib | Upadacitinib | Started Rinvoq at M18 | 15 mg qd | MDA | Y | R.LDA |
| 9 | M | 57 | HDA | HDA | TNF: etanercept, adalimumab | tocilizumab, Sarilumab | Kevzara M6-M9; Tocilizumab M24-ongoing | 200mg Q2W Toci: 162mg qw | HDA | N | LDA |
| | | | | | IL6: tocilizumab | rituximab | Rituxan M12 | 1000mg | HDA | Y | HDA |
| | | | | | CD20; CTLA4; JAKi: Tofacitinib | Upadacitinib, Tocilizumab | Rinvoq M18 | Upa: 15mg qd | HDA | Y | HDA |

FIG. 5C

TREATMENT OF INFLAMMATORY DISORDERS

CROSS REFERENCE TO RELATED APPLICATION

This patent application is a continuation of U.S. patent application Ser. No. 18/730,753, titled "TREATMENT OF INFLAMMATORY DISORDERS," filed on Jul. 19, 2024, which is a national phase application under 35 USC 371 of International Patent Application No. PCT/US2023/061048, titled "TREATMENT OF INFLAMMATORY DISORDERS," filed on Jan. 20, 2023, now International Publication No. WO 2023/141609, which claims priority to U.S. provisional patent application No. 63/266,970, titled "POTENTIATION OF INFLAMMATION INHIBITORY AND IMMUNOSUPPRESSANT DRUGS BY NERVE ACTIVATION," and filed on Jan. 20, 2022, and to U.S. provisional patent application 63/407,588, titled "TREATMENT OF INFLAMMATORY DISORDERS," and filed on Sep. 16, 2022, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Rheumatoid arthritis (RA) is a common chronic inflammatory disease that can lead to substantial loss of physical function due to pain and joint destruction. The underlying mechanisms of the disease involves the body's immune system attacking the joints. Although there is currently no cure for RA, treatments can improve symptoms and slow the progression of the disease. Generally, the goals of treatment are to minimize symptoms such as pain and swelling, to prevent bone and joint destruction, in order to maintain day-to-day functioning and reduce the risk of long term disability. Pain medications, steroids, and non-steroidal anti-inflammatory drugs (NSAIDs) are often used to help relieve symptoms. Disease-modifying antirheumatic drugs (DMARDs) include a wide category of drugs that are used not only to reduce signs and symptoms but also to slow down the progression of RA by reducing and inflammation caused by autoimmune attacks. DMARDs include synthetic drugs and biological drugs. Biological drugs are generally those that are manufactured in, extracted from, or semisynthesized from biological sources. Synthetic DMARDs can be categorized as conventional (csDMARDs) or targeted (tsDMARDs). csDMARDs are drugs that have conventionally been used in the treatment of RA and other inflammatory disorders, while the more recently developed tsDMARDs are targeted to interfere with specific intracellular signaling pathways. Examples of DMARDs include methotrexate, sulfasalazine, leflunomide, hydroxychloroquin, TNF inhibitors (e.g., certolizumab, adalimumab, infliximab and etanercept), abatacept, anakinra, tociluzumab Janus kinase (JAK) inhibitors, and others.

Although medications may help in managing RA and other autoimmune disorders, there are significant drawbacks associated with their chronic use. For example, DMARDs may weaken the body's ability to fight infections, leaving patients at risk of developing serious infections. Medications can also have an associated toxicity depending on the dosage and specific drug reactions by certain patients. Therefore, patients require close monitoring for any suspected toxicity effects, for example, to the kidneys or liver or bone marrow. Further, the effectiveness of some medications may wane over time, which may require administration of higher dosages to reach an effective dose and thereby increasing the risk of serious side effects. In addition, some patients may find certain medications make them feel ill such that they cannot tolerate them. What is needed, therefore, are improved methods for treating RA and other inflammatory and immune disorders compared to pharmaceutical drugs alone.

SUMMARY OF THE DISCLOSURE

The disclosure relates generally to apparatuses (e.g., systems and devices) and methods of nerve stimulation to enhance effectiveness or replace drugs used to inhibit inflammation in the treatment of inflammatory and immune disorders, such as rheumatoid arthritis (RA).

The present invention relates to methods and apparatuses (systems and devices) for treating inflammatory diseases by neurostimulation even in cases where neurostimulation is contraindicated. Surprisingly, the inventors have found that patients who have failed to adequately respond or have become intolerant to a drug therapy (such as a TNF inhibitor) may robustly respond to a treatment regimen (e.g., releasing neurotransmitters that alter the phenotype of immune cells to decrease TNF) to activate a neuroimmune anti-inflammatory pathway. This is surprising because it is believed that treatments that activate the neuroimmune anti-inflammatory pathway rely on the same biological pathway (or pathways) as drug therapy, and therefore would not work in patients for whom the drug is ineffective or has lost effectiveness. Even more surprising, the inventors have found that the treatment regimen described herein may restore the effectiveness of these same drugs in the patient. Described herein are methods and apparatuses (including apparatuses for performing these methods) for reducing inflammation in a patient that is intolerant to or has failed to adequately respond to a particular drug therapy (e.g., TNF inhibition).

For example, described herein are methods of reducing inflammation in a patient that is intolerant to or has failed to adequately respond to TNF inhibition, the method comprising: administering a treatment regimen to activate a neuroimmune anti-inflammatory pathway in the patient that has failed to adequately respond or is intolerant to a TNF inhibitor therapy. For example, a method of reducing inflammation in a patient that is intolerant to or has failed to adequately respond to TNF inhibition may include: identifying that the patient has failed to adequately respond to TNF inhibitor therapy comprising a drug that inhibits TNF; and administering a treatment regimen by applying electrical energy to activate a neuroimmune anti-inflammatory pathway in the patient.

Failure to respond to a particular therapy (e.g., TNF inhibitor therapy, JAK therapy, etc.), in some cases referred to equivalently as failure to adequately respond, means that the patient had insufficient clinical response, for example, either failing to detectably respond at all, or failed to meet established clinical benchmarks, as described herein. For example failure to respond may refer to a change in the DAS28-CRP that is less than the minimal clinically important difference (MCID) deemed to have an implication in clinical management.

The neuroimmune anti-inflammatory pathway may comprises at least one nerve or nerve endings and at least one type of immune cell. Activating the neuroimmune anti-inflammatory pathway in the patient may comprise administering the treatment regimen to one or more nerve targets comprises one or more of: a cranial nerve, a peripheral nerve, a spinal nerve, or a nerve ending within an organ. Activating the neuroimmune anti-inflammatory pathway in the patient may include administering the treatment regimen within the patient's brain. In some examples activating the neuroimmune anti-inflammatory pathway in the patient comprises administering the treatment regimen to one or more of: a vagus nerve, a trigeminal nerve, a splenic nerve, an auricular nerve, or a sacral nerve. Activating the neuroimmune anti-inflammatory pathway in the patient may comprise administering the treatment regimen to a nerve target comprising a peripheral nerve target.

In general, administering the treatment regimen comprises releasing neurotransmitters that alter the phenotype of immune cells to decrease TNF. Releasing neurotransmitters may comprise releasing neurotransmitters that bind to receptors on the immune cells. The neurotransmitters that bind to receptors on the immune cells may be released directly from a stimulated target or by a second nerve that is activated or deactivated through neural-to-neural connections. The neurotransmitters that bind to receptors on the immune cells may be released from a non-neuronal cell. The neurotransmitters released can be one or more of: acetylcholine or norepinephrine or dopamine. The immune cells may be one or more of: monocytes, macrophages, neutrophils, eosinophils, basophils, mast cells, dendritic cells, natural killer cells, B cells or T cells. The neurotransmitters released may bind to one or more of: muscarinic acetylcholine receptors, nicotinic acetylcholine receptors, alpha adrenergic receptors, beta adrenergic receptors, or dopaminergic receptors. The neurotransmitter receptors are one or more of: muscarinic acetylcholine receptors, nicotinic acetylcholine receptors, alpha adrenergic receptors, beta adrenergic receptors, or dopaminergic receptors. In some examples the neurotransmitter receptors are one or more of: M1 acetylcholine receptors, alpha-4 beta-2 nicotinic acetylcholine receptors, alpha-7 nicotinic acetylcholine receptors, alpha adrenergic receptors, beta 2 adrenergic receptors, or dopaminergic receptors.

In particular, administering the treatment regimen may include applying energy to one or more nerve targets. For example, applying energy may include applying one or more of: electrical energy, mechanical energy, and thermal energy. In some examples applying energy comprises applying energy directly through contact or proximity, transdermally applying energy, and/or percutaneously applying energy. In general, applying energy may comprise applying energy with energy steering.

The peripheral nerve target may comprise one or more of: a radial nerve, a median nerve, an ulnar nerve, a femoral nerve, a sciatic nerve, a tibial nerve, a splanchnic nerve, a phrenic nerve, a hepatic nerve, a renal nerve, a splenic nerve, a nerve of the external ear, a greater auricular nerve, a lesser occipital nerve, an auriculotemporal nerve, and an auricular branch of the vagus nerve. The spinal nerve targets may comprise one or more of: a sacral nerve, a cervical nerve, a thoracic nerve and a lumbar nerve.

As mentioned above, activating the neuroimmune anti-inflammatory pathway in the patient may include administering the treatment regimen to one or more nerve targets including nerve ending within an organ. The nerve ending within the organ may be a nerve ending of one or more of: the spleen, the liver, the lymph nodes, the stomach, the small bowel, the large intestine, the pancreas, and the thymus. For example, administering the treatment regimen within the patient's brain may comprise administering the treatment regimen to one or more of: the locus coeruleus, motor nucleus of the vagus nerve, nucleus ambiguus, nucleus basalis, hypothalamus, insula, and basal forebrain.

A peripheral nerve target may comprise one or more of: a radial nerve, a median nerve, an ulnar nerve, a femoral nerve, a sciatic nerve, a tibial nerve, a splanchnic nerve, a phrenic nerve, a hepatic nerve, a renal nerve, a splenic nerve, a nerve of the external ear, a greater auricular nerve, a lesser occipital nerve, an auriculotemporal nerve, or an auricular branch of the vagus nerve. The spinal nerve target may comprise: a sacral nerve, a cervical nerve, a thoracic nerve, a lumbar nerve, or a dorsal root ganglion thereof. The nerve ending within the organ may comprise a nerve ending within one or more of: a spleen, a liver, a lymph node, a stomach, an intestine, a pancreas, or a thymus.

In any of these method administering the treatment regimen may comprise administering a drug that directly or indirectly activates acetylcholine receptors. For example, the drug may comprise an α7nicotinic agonist including (nicotine) and/or an AChE inhibitor. The TNF inhibitor therapy may be one or more of: etanercept, adalimumab, certolizumab pegol, infliximab, golimumab, and biosimilars thereof.

The patient being treated may have an immune or inflammatory disorder (and the methods described herein may be method of treating that disorder). For example, the immune or inflammatory disorder may be ulcerative colitis. The immune or inflammatory disorder may be Crohn's disease. The immune or inflammatory disorder may be one of: rheumatoid arthritis and psoriatic arthritis. The immune or inflammatory disorder may be multiple sclerosis. The immune or inflammatory disorder may be one of: rheumatoid arthritis, bursitis, gouty arthritis, polymyalgia rheumatica, Crohn's disease, ulcerative colitis, multiple sclerosis, coeliac disease, systemic lupus erythematosus, aplastic anemia, myocarditis, spondyloarthritis, inflammatory myositis, alopecia, psoriasis, hay fever, atherosclerosis, asthma, chronic inflammation, chronic prostatitis, glomerulonephritis, nephritis, pelvic inflammatory disease, reperfusion injury, transplant rejection, and vasculitis.

As mentioned, in any of these methods the treatment regimen to activate a neuroimmune anti-inflammatory pathway may be applying electrical energy. For example, applying electrical energy may include applying a plurality of electrical stimulations each having a current no greater than an upper comfort level. The upper comfort level may correspond to a highest current at which the patient is comfortable (e.g., within a range that may be predetermined to be effective.) Any of these methods may include determining the upper comfort level by: administering test stimulations at progressively increasing currents; and associating the upper comfort level to the current at which the patient first feels discomfort. The methods described herein may include determining a threshold current corresponding to a current at which the patient first experiences perception of stimulus. Applying electrical energy may comprise applying nerve stimulations of less than 50 mA (e.g., 50 mA or less, 45 mA or less, 40 mA or less, 35 mA or less, 30 mA or less, 25 mA or less, 20 mA or less, etc.). In some examples applying electrical energy may comprise applying nerve stimulations of 2 mA or less. In some examples applying electrical energy comprises applying nerve stimulations ranging from 20 μA to 200 μA. Applying electrical energy may comprise applying nerve stimulations ranging from 200 μA and 3 mA. Applying electrical energy may comprise applying a charge ranging from 0.2 nanocoulombs and 5 kilocoulomb (e.g., over 5 minutes or less, over 10 minutes or less, over 15 minute or less, over 20 minutes or less, over 30 minutes or less, over 40 minutes or less, over 45 minutes or less, over 1 hours or less, over 1.5 hours or less, over 2 hours or less, over 2.5 hours or less, over 3 hours or less, over 4 hours or less, etc.).

As mentioned, in any of these methods the treatment regimen to activate a neuroimmune anti-inflammatory pathway may be applying mechanical energy (e.g., vibration (haptic) including ultrasound). Applying mechanical energy may comprise applying focused ultrasound within a frequency range 0.1-20 MHz. Applying mechanical energy may comprise applying focused ultrasound within a power range 0.01-10 mW/mm². Applying mechanical energy may comprise applying focused ultrasound within a pressure range of 10-1000 kPa. Applying electromagnetic energy comprise applying electromagnetic induction within a range of 1-500 A/m.

Applying electrical energy may comprise applying electrical energy from an implanted device. The implanted device may contain a pulse generator and at least one lead that terminates with at least one electrode. The electrode may comprise one or more of: a cuff electrode, a thin film electrode, a temperature-dependent form fitting elastomer, and an in situ setting injected conductive material. The at least one electrode may comprise a linear array of electrodes or a nonlinear array of electrodes. The implanted device may be a leadless device comprising a pulse generator and at least one electrode integrated onto the implanted pulse generator. The implanted device may be a transcutaneously powered leaded devices with a receiver that receives, stores, and/or transforms energy delivered from outside the body. The receiver may receive an electrical transmission, including nearfield, midfield, and far field transmissions, at amplitudes between 0.1 uA-500 mA. In some examples, the receiver may receive focused ultrasound energy at frequencies between 0.1-40 MHz and power between 0.01-50 mW/mm² and pressure between 10-1000 kPa. In any of these examples, the receiver may receive energy through electromagnetic induction between 0.1-500 A/m.

The transcutaneously powered leaded device may contain at least one lead that terminates with at least one electrode. In some examples the implanted device comprises a leaded device powered by harvested energy with a receiver that receives, stores, and/or transforms energy from within the body.

As mentioned, the administration of the treatment regimen described herein may surprisingly restore activity of the TNF inhibitor drug that had previously become ineffective. Thus, any of these methods may include administering, concurrent with the administration of the treatment regimen to activate the neuroimmune anti-inflammatory pathway, the same TNF inhibitor therapy that the patient had previously failed to adequately respond to.

The methods and apparatuses described herein may be used to increase the efficacy of an existing ongoing drug treatment. In some examples described herein are methods of applying a treatment regime (e.g., stimulation to activate a neuroimmune anti-inflammatory pathway in the patient) where the patient is continuing treatment with a partially effective drug (e.g., a drug having reduced or waning efficacy). Thus, these methods may restore efficacy to a drug, surprisingly including drugs that are believed to operate in the same biological pathways.

For example, a method of reducing inflammation in a patient that is intolerant to or has failed to adequately respond to either TNF inhibition may include: identifying that the patient has failed to adequately respond to TNF inhibitor therapy comprising a drug that inhibits TNF; administering a treatment regimen to activate a neuroimmune anti-inflammatory pathway in the patient by applying electrical energy to one of: a vagus nerve, a splenic nerve, a radial nerve, a median nerve, an ulnar nerve, a femoral nerve, a sciatic nerve, a tibial nerve, a splanchnic nerve, a phrenic nerve, a hepatic nerve, a renal nerve, a greater auricular nerve, a lesser occipital nerve, or an auriculotemporal nerve, wherein applying electrical energy comprises applying charge ranging from 0.2 nanocoulombs and 5 kilocoulomb per hour.

Applying electrical energy may include applying electrical energy directly, transdermally applying electrical energy, or percutaneously applying electrical energy. In some examples applying energy comprises applying energy with energy steering. Applying electrical energy may include applying to one or more of: the vagus nerve, the splenic nerve, the femoral nerve or the sacral nerve. Applying electrical energy may include applying to one or more of the vagus nerve and the splenic nerve, or a nerve that drive activation of the vagus nerve or splenic nerve. In some examples applying electrical energy comprises applying to one or more nerve ending within an organ in one or more of: the spleen, the liver, the lymph nodes, the stomach, the small bowel, the large intestine, the pancreas, and the thymus. The TNF inhibitor therapy may be one or more of: etanercept, adalimumab, certolizumab pegol, infliximab, golimumab, and biosimilars thereof.

These methods (including methods of applying electrical energy to activate a neuroimmune anti-inflammatory pathway, may be used to treat a patient having an immune or inflammatory disorder. The immune or inflammatory disorder may be one of: rheumatoid arthritis, bursitis, gouty arthritis, polymyalgia rheumatica, Crohn's disease, ulcerative colitis, multiple sclerosis, coeliac disease, systemic lupus erythematosus, aplastic anemia, myocarditis, spondyloarthritis, inflammatory myositis, alopecia, psoriasis, hay fever, atherosclerosis, asthma, chronic inflammation, chronic prostatitis, glomerulonephritis, nephritis, pelvic inflammatory disease, reperfusion injury, transplant rejection, and vasculitis.

Applying electrical energy may include applying a plurality of electrical stimulations each having a current no greater than an upper comfort level. The upper comfort level may correspond to a highest current at which the patient is comfortable. Any of these methods may include determining the upper comfort level by: administering test stimulations at progressively increasing currents; and associating the upper comfort level to the current at which the patient first feels discomfort. Applying electrical energy may comprise applying nerve stimulations of 50 mA or less (e.g., 45 mA or less, 40 mA or less, 35 mA or less, 30 mA or less, 25 mA or less, 20 mA or less, etc.). Applying electrical energy may comprise applying nerve stimulations of 2 mA or less. Applying electrical energy may comprise applying nerve stimulations ranging from 20 μA to 200 μA. Applying electrical energy may comprise applying nerve stimulations ranging from 200 μA and 3 mA. Applying electrical energy may comprise applying electrical energy from an implanted device. The implanted device may contain a pulse generator and at least one lead that terminates with at least one electrode. The electrode may comprise one or more of: a cuff electrode, a thin film electrode, a temperature-dependent form fitting elastomer, and an in situ setting injected conductive material. The at least one electrode may comprise a linear array of electrodes or a nonlinear array of electrodes. In some examples the implanted device is a leadless device comprising a pulse generator and at least one electrode integrated onto the implanted pulse generator. The implanted device may be a transcutaneously powered leaded devices with a receiver that receives, stores, and/or transforms energy delivered from outside the body. The receiver may receive electrical transmission, including nearfield, midfield, and far field transmissions at amplitudes between 0.1 uA-500 mA.

Any of these methods may include administering, concurrent with the application of electrical energy, the same drug, or a drug of the same class that inhibits TNF that the patient had previously failed to adequately respond to.

For example, a method of reducing inflammation in a patient that is intolerant to or has failed to adequately respond to either TNF inhibition may include: identifying that the patient has failed to adequately respond to TNF inhibitor therapy comprising a drug that inhibits TNF; administering a treatment regimen to activate a neuroimmune anti-inflammatory pathway in the patient by applying electrical energy to one of: a vagus nerve, a splenic nerve, a radial nerve, a median nerve, an ulnar nerve, a femoral nerve, a sciatic nerve, a tibial nerve, a splanchnic nerve, a phrenic nerve, a hepatic nerve, a renal nerve, a greater auricular nerve, a lesser occipital nerve, or an auriculotemporal nerve; and administering, concurrent with the application of electrical energy, the same drug, or a drug of the same class that inhibits TNF that the patient had previously failed to adequately respond to.

Although the methods described above are specific to patient's that have failed to adequately respond to TNF inhibitor therapy comprising a drug that inhibits TNF, also described herein are methods of treating patients that are intolerant to or has failed to adequately respond to Janus Kinase (JAK) inhibition by activating a neuroimmune anti-inflammatory pathway in the patient that has failed to adequately respond or is intolerant to a JAK inhibitor therapy. This is also surprising, as it is currently believed that drugs to treat inflammation by JAK inhibition are using the same or overlapping pathway as activation of the neuroinflammatory pathway. For example, described herein are methods of reducing inflammation in a patient that is intolerant to or has failed to adequately respond to Janus Kinase (JAK) inhibition, the method comprising: administering a treatment regimen to activate a neuroimmune anti-inflammatory pathway in the patient that has failed to adequately respond or is intolerant to a JAK inhibitor therapy. For example, a method of reducing inflammation in a patient that is intolerant to or has failed to adequately respond to Janus Kinase (JAK) inhibition, may include: identifying that the patient has failed to adequately respond to a JAK inhibitor therapy comprising a drug that inhibits JAK; and administering a treatment regimen by applying electrical energy to activate a neuroimmune anti-inflammatory pathway in the patient.

The neuroimmune anti-inflammatory pathway may include at least one nerve or nerve endings and at least one type of immune cell. Administering the treatment regimen may comprise applying energy to one or more nerve targets. For example, applying energy may comprise applying one or more of: electrical energy, mechanical energy, and thermal energy. Applying energy may include applying energy directly through contact or proximity, transdermally applying energy, or percutaneously applying energy. In any of these examples, applying energy comprises applying energy with energy steering.

In any of these methods, activating the neuroimmune anti-inflammatory pathway in the patient may include administering the treatment regimen to one or more nerve targets comprises one or more of: a cranial nerve, a peripheral nerve, a spinal nerve, or a nerve ending within an organ. Activating the neuroimmune anti-inflammatory pathway in the patient may include administering the treatment regimen within the patient's brain. In some examples activating the neuroimmune anti-inflammatory pathway in the patient comprises administering the treatment regimen to one or more of: a vagus nerve, a trigeminal nerve, a glossopharyngeal nerve, an optic nerve, or a facial nerve. Activating the neuroimmune anti-inflammatory pathway in the patient may include administering the treatment regimen to a nerve targets comprising a peripheral nerve target, such as one or more of: a radial nerve, a median nerve, an ulnar nerve, a femoral nerve, a sciatic nerve, a tibial nerve, a splanchnic nerve, a phrenic nerve, a hepatic nerve, a renal nerve, a splenic nerve, a nerve of the external ear, a greater auricular nerve, a lesser occipital nerve, an auriculotemporal nerve, and an auricular branch of the vagus nerve. The spinal nerve targets may include one or more of: a sacral nerve, a cervical nerve, a thoracic nerve and a lumbar nerve. The nerve ending within the organ may be a nerve ending of one or more of: the spleen, the liver, the lymph nodes, the stomach, the small bowel, the large intestine, the pancreas, and the thymus. In any of these examples administering the treatment regimen within the patient's brain may include administering the treatment regimen to one or more of: the locus coeruleus, motor nucleus of the vagus nerve, nucleus ambiguus, nucleus basalis, hypothalamus, and basal forebrain. The peripheral nerve target may include one or more of: a radial nerve, a median nerve, an ulnar nerve, a femoral nerve, a sciatic nerve, a tibial nerve, a splanchnic nerve, a phrenic nerve, a hepatic nerve, a renal nerve, a splenic nerve, a nerve of the external ear, a greater auricular nerve, a lesser occipital nerve, an auriculotemporal nerve, or an auricular branch of the vagus nerve. The spinal nerve target may comprise: a sacral nerve, a cervical nerve, a thoracic nerve, a lumbar nerve, or a dorsal root ganglion thereof. The nerve ending within the organ may comprise a nerve ending within one or more of: a spleen, a liver, a lymph node, a stomach, an intestine, a pancreas, or a thymus.

The JAK inhibitor therapy may be one or more of: baricitinib, tofacitinib, upadacitinib, filgotinib, ruxolitinib, oclacitinib, peficitinib, fedratinib, delgocitinib, abrocitinib, deucravacitinib, and biosimilars thereof.

These methods may be used to treat a patient having an immune or inflammatory disorder. For example, the patient may have ulcerative colitis. In some examples the immune or inflammatory disorder is Crohn's disease. In some examples the immune or inflammatory disorder is one of: rheumatoid arthritis and psoriatic arthritis. The immune or inflammatory disorder may be multiple sclerosis. The immune or inflammatory disorder may be one of: rheumatoid arthritis, bursitis, gouty arthritis, polymyalgia rheumatica, Crohn's disease, ulcerative colitis, multiple sclerosis, celiac disease, systemic lupus erythematosus, aplastic anemia, myocarditis, spondyloarthritis, inflammatory myositis, alopecia, psoriasis, hay fever, atherosclerosis, asthma, chronic inflammation, chronic prostatitis, glomerulonephritis, nephritis, pelvic inflammatory disease, reperfusion injury, transplant rejection, and vasculitis.

In any of these methods applying electrical energy may include applying a plurality of electrical stimulations each having a current no greater than an upper comfort level. For example, the upper comfort level may correspond to a highest current at which the patient is comfortable. These methods may include determining the upper comfort level by: administering test stimulations at progressively increasing currents; and associating the upper comfort level to the current at which the patient first feels discomfort. Any of these methods may include determining a threshold current corresponding to a current at which the patient first experiences perception of stimulus.

As mentioned above, in any of these methods, applying electrical energy may include applying nerve stimulations of 50 mA or less (e.g., 50 mA or less, 45 mA or less, 40 mA or less, 35 mA or less, 30 mA or less, 25 mA or less, 20 mA or less, etc.). Applying electrical energy may comprise applying nerve stimulations of less than 2 mA. In some examples applying electrical energy comprises applying nerve stimulations ranging from 20 µA to 200 µA. Applying electrical energy may comprise applying nerve stimulations ranging from 200 µA and 3 mA. Applying electrical energy may comprise applying a charge ranging from 0.2 nanocoulombs and 5 kilocoulomb (e.g., over 5 minutes or less, over 10 minutes or less, over 15 minute or less, over 20 minutes or less, over 30 minutes or less, over 40 minutes or less, over 45 minutes or less, over 1 hours or less, over 1.5 hours or less, over 2 hours or less, over 2.5 hours or less, over 3 hours or less, over 4 hours or less, over 1 day or less, etc.).

Applying mechanical energy may include applying focused ultrasound within a frequency range 0.1-20 MHz. Applying mechanical energy may comprise applying focused ultrasound within a power range 0.01-10 mW/mm². Applying mechanical energy may comprise applying focused ultrasound within a pressure range of 10-1000 kPa.

Applying electromagnetic energy may comprises applying electromagnetic induction within a range of 1-500 A/m.

Applying electrical energy may comprise applying electrical energy from an implanted device. The implanted device may contain a pulse generator and at least one lead that terminates with at least one electrode. The electrode may comprise one or more of: a cuff electrode, a thin film electrode, a temperature-dependent form fitting elastomer, and an in situ setting injected conductive material. The at least one electrode may comprise a linear array of electrodes or a nonlinear array of electrodes. The implanted device may be a leadless device comprising a pulse generator and at least one electrode integrated onto the implanted pulse generator. In some examples the implanted device is a transcutaneously powered leaded devices with a receiver that receives, stores, and/or transforms energy delivered from outside the body. The receiver may receive electrical transmission, including nearfield, midfield, and far field transmissions at amplitudes between 0.1 uA-500 mA. The receiver may receive focused ultrasound energy at frequencies between 0.1-40 MHz and power between 0.01-50 mW/mm² and pressure between 10-1000 kPa. The receiver may receive energy through electromagnetic induction between 0.1-500 A/m.

The transcutaneously powered leaded device may contain at least one lead that terminates with at least one electrode. In some examples the implanted device comprises a leaded device powered by harvested energy with a receiver that receives, stores, and/or transforms energy from within the body.

The JAK inhibitor therapy may inhibit activity of one or more of JAK1, JAK2, JAK3, and TYK2.

Any of these methods may include administering, concurrent with the administration of the treatment regimen to activate the neuroimmune anti-inflammatory pathway, the same JAK inhibitor therapy that the patient had previously failed to adequately respond to.

For example, a method of reducing inflammation in a patient that is intolerant to or has failed to adequately respond to Janus Kinase (JAK) inhibition may include: identifying that the patient has failed to adequately respond to a JAK inhibitor therapy comprising a drug that inhibits JAK; administering a treatment regimen to activate a neuroimmune anti-inflammatory pathway in the patient by applying electrical energy to one of: a vagus nerve, a splenic nerve, a radial nerve, a median nerve, an ulnar nerve, a femoral nerve, a sciatic nerve, a tibial nerve, a splanchnic nerve, a phrenic nerve, a hepatic nerve, a renal nerve, a greater auricular nerve, a lesser occipital nerve, or an auriculotemporal nerve, wherein applying electrical energy comprises applying charge ranging from 0.2 nanocoulombs and 5 kilocoulomb per hour.

The patient may be intolerant to or may have failed to adequately respond to Janus Kinase (JAK) inhibition wherein the JAK inhibitor therapy inhibits activity of one or more of JAK1, JAK2, JAK3, and TYK2. As mentioned above, applying electrical energy may comprise applying electrical energy directly, transdermally applying electrical energy, or percutaneously applying electrical energy. Applying energy may include applying energy with energy steering. Applying electrical energy may include applying to one or more of: the vagus nerve, the splenic nerve, the femoral nerve or the sacral nerve.

Applying electrical energy may include applying to one or more of the vagus nerve and the splenic nerve, or a nerve that drive activation of the vagus nerve or splenic nerve.

In any of these methods, applying electrical energy may include applying to one or more nerve ending within an organ in one or more of: the spleen, the liver, the lymph nodes, the stomach, the small bowel, the large intestine, the pancreas, and the thymus.

The JAK inhibitor therapy may be one or more of: baricitinib, tofacitinib, upadacitinib, filgotinib, ruxolitinib, oclacitinib, peficitinib, fedratinib, delgocitinib, abrocitinib, deucravacitinib. The patient may have an immune or inflammatory disorder. For example, the immune or inflammatory disorder may be one of: rheumatoid arthritis, bursitis, gouty arthritis, polymyalgia rheumatica, Crohn's disease, ulcerative colitis, multiple sclerosis, coeliac disease, systemic lupus erythematosus, aplastic anemia, myocarditis, spondyloarthritis, inflammatory myositis, alopecia, psoriasis, hay fever, atherosclerosis, asthma, chronic inflammation, chronic prostatitis, glomerulonephritis, nephritis, pelvic inflammatory disease, reperfusion injury, transplant rejection, and vasculitis.

Applying electrical energy may comprise applying a plurality of electrical stimulations each having a current no greater than an upper comfort level. The upper comfort level may correspond to a highest current at which the patient is comfortable. Any of these methods may include determining the upper comfort level by: administering test stimulations at progressively increasing currents; and associating the upper comfort level to the current at which the patient first feels discomfort. Applying electrical energy may include applying nerve stimulations of 50 mA or less (e.g., 50 mA or less, 45 mA or less, 40 mA or less, 35 mA or less, 30 mA or less, 25 mA or less, 20 mA or less, etc.). For example, applying electrical energy may include applying nerve stimulations of less than 2 mA. Applying electrical energy may comprise applying nerve stimulations ranging from 20 µA to 200 µA. Applying electrical energy may comprise applying nerve stimulations ranging from 200 µA and 3 mA. Applying electrical energy may comprise applying electrical energy from an implanted device. The implanted device may contain a pulse generator and at least one lead that terminates with at least one electrode. In some examples the electrode comprises one or more of: a cuff electrode, a thin film electrode, a temperature-dependent form fitting elastomer, and an in situ setting injected conductive material. The at least one electrode may comprise a linear array of electrodes or a nonlinear array of electrodes. In any of these methods, the implanted device may be a leadless device comprising a pulse generator and at least one electrode integrated onto the implanted pulse generator. The implanted device may be a transcutaneously powered leaded devices with a receiver that receives, stores, and/or transforms energy delivered from outside the body. The receiver may receive electrical transmission, including nearfield, midfield, and far field transmissions at amplitudes between 0.1 uA-500 mA.

Any of these methods may include administering, concurrent with the application of electrical energy, the same drug, or a drug of the same class that inhibits JAK that the patient had previously failed to adequately respond to.

For example, a method of reducing inflammation in a patient that is intolerant to or has failed to adequately respond to Janus Kinase (JAK) inhibition may include: identifying that the patient has failed to adequately respond to a JAK inhibitor therapy comprising a drug that inhibits JAK; administering a treatment regimen to activate a neuroimmune anti-inflammatory pathway in the patient by applying electrical energy to one of: a vagus nerve, a splenic nerve, a radial nerve, a median nerve, an ulnar nerve, a femoral nerve, a sciatic nerve, a tibial nerve, a splanchnic nerve, a phrenic nerve, a hepatic nerve, a renal nerve, a greater auricular nerve, a lesser occipital nerve, or an auriculotemporal nerve; and administering, concurrent with the application of electrical energy, the same drug, or a drug of the same class that inhibits JAK that the patient had previously failed to adequately respond to.

In any of these methods described above, the neurostimulation can be administered according to a nerve stimulation regimen that includes applying a number of nerve stimulations doses to the patient over a period of time. The nerve stimulation regimen may be administered before, during, or after administration of one or more doses of the drug(s). The methods and apparatuses described herein may be useful in treating inflammation associated with rheumatoid arthritis (RA). In some cases, the methods and apparatuses may also be useful in treating other inflammatory and/or immune conditions such as Crohn's disease, ulcerative colitis, multiple sclerosis, coeliac disease, systemic lupus erythematosus, myocarditis, spondyloarthritis, inflammatory myositis, alopecia, psoriasis, hay fever, atherosclerosis, asthma, chronic inflammation, chronic prostatitis, glomerulonephritis, nephritis, pelvic inflammatory disease, reperfusion injury, transplant rejection, vasculitis.

The nerve stimulation treatments described herein may be combined with administration of one or more drugs used to reduce inflammation. In some examples, the drug(s) include one or more immunosuppressant and/or inflammation inhibitory drugs. In some cases, immunosuppressant drug(s) may include one or more disease-modifying antirheumatic drugs (DMARDs). The DMARD(s) can include synthetic drug(s) and/or a biological drug(s). The DMARD(s) can be conventional (csDMARDs) and/or targeted (tsDMARDs). The drug(s) may include one or more enzyme inhibitors (e.g., Janus kinase (JAK) inhibitors), recombinant proteins, vaccines, blood products, gene therapy drugs, antibodies (e.g., monoclonal antibodies), small molecule drugs, and/or cell therapy drugs. In some cases, the drug(s) may be a glucocorticoid, such as prednisone, dexamethasone, and/or hydrocortisone. In some cases the drug(s) may be hydroxychloroquine and/or methotrexate (MTX).

Other drugs may include drugs for Crohn's, such as one or more of: steroids (e.g., beclomethasone dipropionate, budesonide, hydrocortisone, methylprednisolone, prednisolone, prednisone), anti-inflammatory drugs (e.g., balsalazide, mesalamine, olsalazine, sulfasalazine), immunosuppressants (e.g., azathioprine, cyclosporin, mercaptopurine, methotrexate, mycophenolate mofetil, tacrolimus), antibacterial drugs (e.g., ciprofloxacin, metronidazole, rifaximin, vancomycin), biologics and (e.g., adalimumab, infliximab, ustekinumab, vedolizumab). Other drugs may also include drugs for ulcerative colitis, such as one or more of: 5-aminosalicylic acid (5-ASA), balsalazide, mesalamine, olsalazine, sulfasalazine, corticosteroids, immunosuppressants (e.g., 6-mercaptopurine (6-MP), azathioprine, cyclosporine, tacrolimus), biologics (e.g., adalimumab, plus adalimumab-atto, adalimumab-adbm (biosimilars), certolizumab pegol, golimumab, infliximab, ustekinumab, vedolizumab, etc.), tofacitinib, sphingosine 1-phosphate (S1P) receptor modulators, an ozanimod. Other drugs may also include drugs for multiple sclerosis (MS) such as one or more of: Avonex® (interferon beta-1a), Betaseron® (interferon beta-1b), Copaxone® (glatiramer acetate), Extavia® (interferon beta-1b), Glatiramer Acetate Injection (glatiramer acetate-generic equivalent of Copaxone 20 mg and 40 mg doses), Glatopa® (glatiramer acetate-generic equivalent of Copaxone 20 mg and 40 mg doses), Kesimpta® (ofatumumab), Plegridy® (peginterferon beta-1a), Rebif® (interferon beta-1a), Aubagio® (teriflunomide), Bafiertam™ (monomethyl fumarate), Dimethyl Fumarate (dimethyl fumarate-generic equivalent of Tecfidera), Gilenya® (fingolimod), Mavenclad® (cladribine), Mayzent® (siponimod), Ponvory™ (ponesimod), Tecfidera® (dimethyl fumarate), Vumerity® (diroximel fumarate), Zeposia® (ozanimod), Lemtrada® (alemtuzumab), Novantrone® (mitoxantrone), Ocrevus® (ocrelizumab), Tysabri® (natalizumab).

Other drugs may also include drugs for psoriatic arthristus (PsA), such as one or more of: etanercept, secukinumab, ustekinumab, adalimumab, infliximab, ixekizumab, guselkumab, risankizumab, certolizumab, abatacept, golimumab, adalimumab, upadacitinib, tofacitinib, sulfasalazine, leflunomide, methotrexate, azathioprine, dexamethasone, prednisone, cortisone, apremilast, mycophenolate mofetil, triamcinolone, corticotropin, cyclosporine, hydroxyurea, acitretin, auranofin.

Nerve stimulation in combination with administration of a drug may allow for decreased dosing of the drug. For example, a first dosage of a drug administered to the patient may be found to inadequately treat a patient's symptoms. A nerve stimulation treatment regimen may be co-administered with the drug at the first dosage to potentiate the drug and effectively treat the patient's symptoms. In some cases, the co-administration of the nerve stimulation may allow for administration of a second dosage, which is less than the first dosage, to effectively treat the patient's symptoms. The co-administration of nerve stimulation and drug therapy may result in better treatment than nerve stimulation alone or drug therapy alone.

In some cases, the dosage of a drug can be tapered when concurrently implemented with nerve stimulation, thereby improving safety and/or minimizing unwanted effects associated with the drug. For example, when on a nerve stimulation therapy, a drug may be tapered by administering it less frequently and/or at a lower concentration. In some cases, the patient may be weaned off the drug altogether.

In some cases, a nerve stimulation regimen may be implemented to effectively treat a patient's symptoms after it has been determined that drug treatment has been unsuccessful, for example, as described above for TNF inhibitor drugs. For example, a method of reducing inflammation in a patient may include determining that administration of a drug on the patient has failed to achieve or to maintain a low disease activity state in the patient and administering a nerve stimulation treatment regimen to achieve the low disease activity state.

A nerve stimulation prescription can be added to a concurrently taken biological or targeted synthetic therapy, or biological or targeted synthetic therapy can be added to an active nerve stimulation treatment prescription, regardless of prior drug exposure.

In some examples, nerve stimulation therapy can reactivate responsivity to a drug in a patient who previously lacked or lost a clinical response to the drug.

In some examples, nerve stimulation therapy can be implemented as an add-on to a drug therapy to improve or extend the clinical efficacy of the drug therapy.

In some cases, a nerve stimulation regimen may be implemented if a patient is determined not to have undergone treatment using a particular drug, or particular class of drugs. For example, a method of reducing inflammation can include determining that the patient has not been treated with a particular drug and applying a nerve stimulation regimen to achieve a low disease activity state in the patient.

For example, the clinical efficacy of nerve stimulation in patients that are naïve to a JAK inhibitor can be superior to nerve stimulation to those with prior JAK inhibitor exposure.

One aspect of the disclosure is a method of reducing inflammation in a patient, the method including: determining that administration of an immunosuppressant drug on the patient has failed to achieve or to maintain a low disease activity state in the patient; and administering a nerve stimulation treatment regimen to achieve the low disease activity state, as described herein.

In this aspect, the method may further include: determining a first dosage that the immunosuppressant drug was administered to the patient prior to administering the nerve stimulation; and wherein administering the nerve stimulation treatment regimen includes concurrently administrating the nerve stimulation treatment regimen and the immunosuppressant drug, wherein the immunosuppressant drug is administered at a second dosage that is less than the first dosage. In this aspect, concurrently administrating the nerve stimulation treatment regimen and the immunosuppressant drug may include administering one type (or more than one type) of immunosuppressant drug.

The nerve stimulation treatment regimen may include a plurality of electrical stimulations each having a current no greater than an upper comfort level. The upper comfort level may correspond to a highest current at which the patient is comfortable.

The method may further include determining the upper comfort level by: administering test stimulations at progressively increasing currents; and associating the upper comfort level to the current at which the patient first feels discomfort.

The method may further include determining a threshold current corresponding to a current at which the patient first experiences perception of stimulus.

The nerve stimulation treatment regimen may include applying nerve stimulations of less than 10 mA. The nerve stimulation treatment regimen may include applying nerve stimulations of less than 2 mA.

The nerve stimulation treatment regimen may include applying nerve stimulations ranging from 20 μA to 200 μA.

The nerve stimulation treatment regimen may include applying nerve stimulations ranging from 200 μA and 2 mA.

The nerve stimulation treatment regimen may include applying a charge ranging from 0.2 nanocoulombs and 5 kilocoulomb.

In this aspect, the immunosuppressant drug may include a disease-modifying antirheumatic drug (DMARD). The DMARD may include one or more of a biological DMARD and a synthetic DMARD. The DMARD may include one or more of a conventional DMARD and a targeted DMARD. The immunosuppressant drug may include one or more of a Janus kinase (JAK) inhibitor and a phosphodiesterase 4 (PDE4) inhibitor.

The immunosuppressant drug may be a biological drug including one or more of etanercept, adalimumab, tocilizumab, abatacept, certolizumab, infliximab, rituximab, golimumab, and a biosimilar thereof.

The immunosuppressant drug may be a non-biologic drug including one or more of ciclosporin, cyclophosphamide, hydroxychloroquine, leflunomide, methotrexate, mycophenolate, and sulfasalazine. The immunosuppressant drug may be a biological drug. The immunosuppressant drug may be a corticotropin (e.g., ACTHAR™ gel)

The method may further include administering a nonbiological drug to the patient during administration of the nerve stimulation treatment regimen.

The non-biologic drug may include a steroid. The steroid may include a glucocorticoid. The non-biologic drug may include a nonsteroidal anti-inflammatory drug (NSAID).

The patient may have an immune or inflammatory disorder. The immune or inflammatory disorder may be an autoimmune disorder. The immune or inflammatory disorder may be one or more of rheumatoid arthritis, bursitis, gouty arthritis, polymyalgia rheumatica, Crohn's disease, ulcerative colitis, multiple sclerosis, coeliac disease, systemic lupus erythematosus, aplastic anemia, myocarditis, spondyloarthritis, inflammatory myositis, alopecia, psoriasis, hay fever, atherosclerosis, asthma, chronic inflammation, chronic prostatitis, glomerulonephritis, nephritis, pelvic inflammatory disease, reperfusion injury, transplant rejection, vasculitis, and myocarditis.

Applying the nerve stimulation may include applying the nerve stimulation to one or more of the vagus nerve, the splenic nerve, and the sacral nerve. Nerve stimulation treatment regimen may be administered using an implanted device. Nerve stimulation treatment regimen may include transdermally applying nerve stimulation.

One aspect of the disclosure includes methods of potentiating an immunosuppressant drug in the treatment of an inflammatory disorder in a patient, the method including: co-administrating an immunosuppressant drug therapy regimen and a nerve stimulation regimen on the patient to achieve a low disease activity state in the patient, wherein the immunosuppressant drug therapy regimen includes administration of one or more doses of the immunosuppressant drug, and wherein the nerve stimulation regimen includes administration of a plurality of electrical nerve stimulations. As discussed above, the co-administered drug may be one in which the patient had previously shown little or no (or attenuated/reduced) clinical effect (e.g., a TNF inhibitor, such as certolizumab, adalimumab, infliximab and etanercept, a JAK inhibitor, etc.).

Any of these nerve stimulation regimen may be administered using an implanted device. The nerve stimulation regimen may include transdermally applying the plurality of electrical nerve stimulations. The inflammatory disorder may be one or more of rheumatoid arthritis, bursitis, gouty arthritis, polymyalgia rheumatica, Crohn's disease, ulcerative colitis, multiple sclerosis, coeliac disease, systemic lupus erythematosus, aplastic anemia, myocarditis, spondyloarthritis, inflammatory myositis, alopecia, psoriasis, hay fever, atherosclerosis, asthma, chronic inflammation, chronic prostatitis, glomerulonephritis, nephritis, pelvic inflammatory disease, reperfusion injury, transplant rejection, vasculitis, and myocarditis.

These methods may further include administering a non-biologic drug to the patient during co-administration of the biological drug and the nerve stimulation regimen (e.g., one or more of ciclosporin, cyclophosphamide, hydroxychloroquine, leflunomide, methotrexate, mycophenolate, and sulfasalazine).

The low disease activity state may be determined by a standard method of quantifying symptoms of the patient. A standard method of quantifying symptoms of the patient may include one or more of the Disease Activity Score-28 for rheumatoid arthritis (DAS28-CRP/ESR) and the Clinical Disease Activity Index (CDAI), SDAI, RAPID-3, HAQ-DI, RADAI. A low disease activity state may be determined by measuring one or more biomarkers.

A method of treating a patient with an immune disorder may including: determining that the patient has failed to achieve a low disease state using administration of a first immunosuppressant drug; and co-administrating a nerve stimulation regimen with an immunosuppressant drug therapy regimen to achieve the low disease activity state in the patient, wherein the nerve stimulation regimen includes administration of a plurality of electrical nerve stimulations. The immune disorder may be one or more of rheumatoid arthritis, Crohn's disease, multiple sclerosis, coeliac disease, systemic lupus erythematosus, aplastic anemia, myocarditis, spondyloarthritis, inflammatory myositis, alopecia, psoriasis, hay fever, atherosclerosis, asthma, chronic inflammation, chronic prostatitis, glomerulonephritis, nephritis, pelvic inflammatory disease, reperfusion injury, transplant rejection, vasculitis.

The neurostimulation methods described herein can be adapted to activate the cholinergic anti-inflammatory pathway (NCAP). The nerve stimulation may be administered by an implanted device or may be administered transdermally. In the case of an implanted device, the device may include one or more electrodes that deliver stimulation directly to one or more nerves. In the case of transdermal administration, a transcutaneous electrical nerve stimulation (TENS) device or a focused ultrasound energy device may be adapted to deliver electrical stimulation to stimulate one or more nerves sufficient to activate the cholinergic anti-inflammatory pathway. In some cases, the device(s) is/are configured to administer stimulation according to a prescribed dosage regimen, as described herein.

In some examples, the methods can be implemented by a microstimulator implanted within the patient proximate to one or more nerves, such as a vagus nerve, the sacral nerve, and/or a splenic nerve. A microstimulator can include a controller adapted to deliver electrical stimulation doses at preset times (e.g., throughout the day or week) or as dictated by a user of the device (e.g., on-demand).

The apparatuses (devices and systems) and methods of using them described herein may incorporate some or all of the features of microstimulators, nerve cuffs ("PODs"), chargers, and programmer/controllers described herein may be similar or identical to those described in International Patent Application Publication No. WO 2011/028763, titled "PRESCRIPTION PAD FOR TREATMENT OF INFLAMMATORY DISORDERS;" U.S. Patent Application Publication No. US-2010-0312320-A1, titled "NERVE CUFF WITH POCKET FOR LEADLESS STIMULATOR;" and U.S. Pat. No. 9,993,651, titled "NEURAL STIMULATION DEVICES AND SYSTEMS FOR TREATMENT OF CHRONIC INFLAMMATION," each of which is herein incorporated by reference in its entirety.

Any of the methods and apparatuses described herein may involve vagus nerve stimulation (VNS) to reduce of inflammation through activation of the cholinergic anti-inflammatory pathway. Any portion of the vagus nerve may be stimulated. In some examples, particular benefit is found when the sub-diaphragmatic vagus nerve and/or the cervical vagus nerve is stimulated.

Treatment and devices for treating inflammation by vagus nerve stimulation has been described, for example, in U.S. Pat. Nos. 6,838,471, 8,914,114, 9,211,409, 6,610,713, 8,412,338, 8,996,116, 8,612,002, 9,162,064, 8,855,767, 8,886,339, 9,174,041, 8,788,034, 9,211,410, and 9,993,651 and in International Patent Publication Nos. WO2016183353A1 and WO2017127758A1, each of which is herein incorporated herein by reference in its entirety.

These and other aspects and advantage are described herein.

BRIEF DESCRIPTION OF THE DRAWINGS

FIG. 1 shows clinical results from a subject with RA who had a lack of efficacy to a TNF-targeted therapy prior to starting nerve stimulation.

FIG. 2 shows clinical results from a subject with Crohn's disease who had a lack of efficacy to a TNF-targeted therapy prior to starting nerve stimulation.

FIG. 3 shows clinical results from a subject with RA who had a lack of efficacy to a JAK-targeted therapy prior to starting nerve stimulation.

FIGS. 4A-4B show a table summarizing patient response data as described herein.

FIGS. 5A-5C show a table summarizing patient response data as described herein.

DETAILED DESCRIPTION

Figure 2:
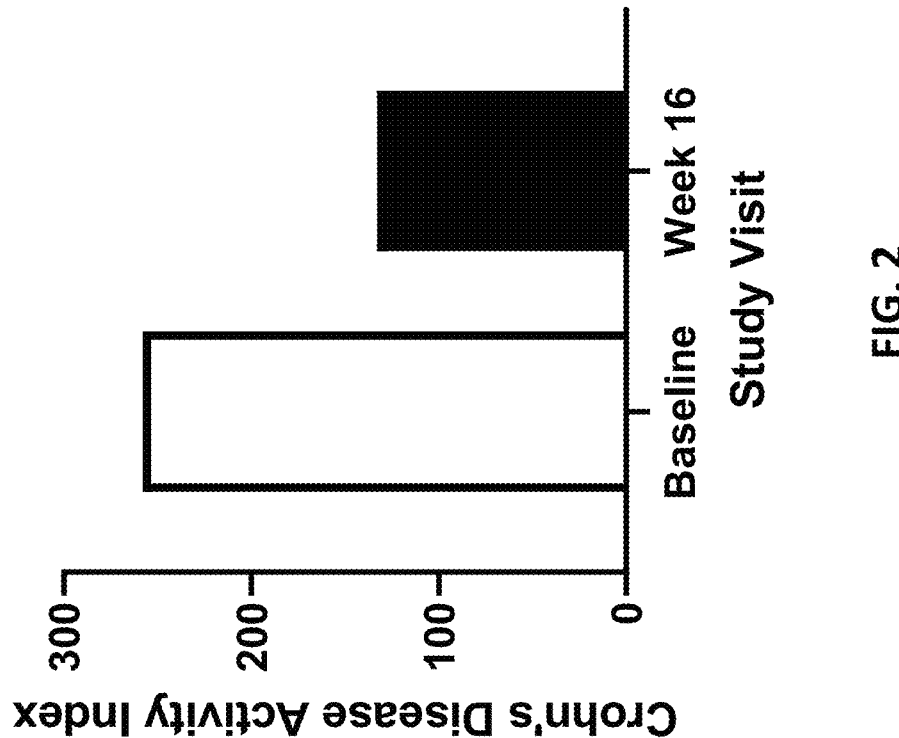
FIGS. 1-3 are graphs showing clinical results of subjects treated with neuroimmune pathway modulation through nerve stimulation in the treatment of rheumatoid arthritis (RA) or Crohn's disease symptoms that had previous exposure to and lack of efficacy to a TNF or JAK targeted therapy.

Described herein are methods and apparatuses (e.g., devices and systems) for nerve stimulation to treat inflammatory and autoimmune conditions, such as, but not limited to, rheumatoid arthritis (RA) or Crohn's disease. In particular, described herein is nerve stimulation to treat an inflammatory disorder in patients that are intolerant to, or have failed to adequately respond to, tumor necrosis factor (TNF or sometimes referred to as TNF-α) inhibition. For example, these patients typically failed to adequately respond (above a clinical threshold) to a TNF inhibitor therapy including none or more of: etanercept, adalimumab, certolizumab pegol, infliximab, golimumab, and biosimilars thereof. Surprisingly, the methods and apparatuses described herein for treating a patient believed to be resistant to TNF inhibition therapy is given a treatment regimen to activate a TNF dependent neuroimmune anti-inflammatory pathway (e.g., by the application of electrical, mechanical and/or thermal energy) may result in a significant therapeutic benefit. Further, these methods and apparatuses may restore previously attenuated responses to TNF inhibition pharmaceutical agents. It has long been presumed that treatment regimens, including, e.g., vagus nerve stimulation, would also be ineffective in these patients, since it is thought that the same biological pathways are involved in both pharmaceutical TNF inhibition as in activation of a neuroimmune anti-inflammatory pathway by the application of energy. Specifically, it has long been believed that a patient who has fails to adequately respond substantially to TNF inhibitors would not be benefit from alternative treatments that also block TNF signaling.

The application of energy (e.g., electrical, mechanical or thermal energy) to activate the neuroimmune anti-inflammatory pathway is believed to include the release of TNF; for example, the application of energy to the vagus nerve, trigeminal nerve, or other nerve of the neuroimmune anti-inflammatory pathway (e.g., the glossopharyngeal nerve, optic nerve, or facial nerve(s)) to reduce inflammation reduces release of TNF from immune cells. It is therefore quite surprising that using energy to activate the neuroimmune anti-inflammatory pathway results in a therapeutic benefit in clinical trial subjects that have previously not been adequately treated by TNF inhibitors.

For example, the application electrical energy to activate the neuroimmune anti-inflammatory pathway by stimulation of the vagus nerve with enough energy to depolarize neurons and cause an action potential activates neuroimmune pathways. These neuroimmune pathways utilize both nerves and immune cells, using neurotransmitters to communicate (Tracey (2002), "The inflammatory reflex," *Nature* 420 (6917): 853-859), and lead to reduction of TNF in immune cells in organs such as the blood, liver, lung, spleen, kidneys, gut and heart (Borovikova et al. (2000), "Vagus nerve stimulation attenuates the systemic inflammatory response to endotoxin," *Nature* 405:458-462; Tracey (2002); Olofsson et al. (2015), "Single-pulse and unidirectional electrical activation of the cervical vagus nerve reduces tumor necrosis factor in endotoxemia," *Bioelectronic Medicine:* 37-42). The neuroimmune anti-inflammatory pathway (which may also be referred to as the inflammatory reflex) includes the cholinergic anti-inflammatory pathway and the intestinal cholinergic anti-inflammatory pathway. The cholinergic anti-inflammatory pathway involves the splenic nerve and the spleen (Olofsson et al. (2012), "Rethinking inflammation: neural circuits in the regulation of immunity," *Immunological Reviews* 248(1): 188-204) while the intestinal cholinergic anti-inflammatory pathway is spleen independent (Caravaca et al. (2022), "Vagus Nerve Stimulation Reduces Indomethacin-Induced Small Bowel Inflammation, " *Frontiers in Neuroscience* 15(1842)).

TNF is an important cytokine in the pathogenesis and pathophysiology of many inflammatory diseases, including rheumatoid arthritis, psoriatic arthritis, Crohn's disease, and ulcerative colitis. Indeed, several therapies targeting TNF to decrease its bioavailability have been demonstrated effective and are currently marketed for the treatment of these and other diseases (Monaco et al. (2015), "Anti-TNF therapy: past, present and future," Int Immunol 27(1): 55-62). VNS has been demonstrated to reduce TNF in immune cells and serum and therapeutic in rheumatoid arthritis (Koopman et al. (2016); Genovese et al. (2020)).

Thus, a patient who has previously not had an adequate clinical response to TNF inhibitors would not be expected to benefit from other treatments that also block TNF signaling. This is supported by multiple published studies showing that treating a patient that has failed to response to a particular TNF inhibitor (drug) with another TNF inhibitor has a significantly lower expected therapeutic potential across all of the clinical parameters studied (Rendas-Baum et al., (2011), "Evaluating the efficacy of sequential biologic therapies for rheumatoid arthritis patients with an inadequate response to tumor necrosis factor-alpha inhibitors," *Arthritis Research & Therapy* 13: R25). Further, it has been shown that treating a patient that has insufficient response to a first anti-TNF drug with a non-anti-TNF drug (another class of drug) results in a significantly better response than treating with a second anti-TNF drug (Emery et al. (2015), "Rituximab versus an alternative TNF inhibitor in patients with rheumatoid arthritis who failed to adequately respond to a single previous TNF inhibitor: SWITCH-RA, a global, observational, comparative effectiveness study," *Ann Rheum Dis* 74(6): 979-984; Gottenberg et al. (2016), "Non-TNF-Targeted Biologic vs a Second Anti-TNF Drug to Treat Rheumatoid Arthritis in Patients With Insufficient Response to a First Anti-TNF Drug: A Randomized Clinical Trial," *JAMA* 316(11): 1172-1180; Choi et al. (2021) "Association of first, second, and third-line bDMARDs and tsDMARD with drug survival among seropositive rheumatoid arthritis patients: Cohort study in A real world setting," *Semin Arthritis Rheum* 51(4): 685-691). It is therefore quite surprising that, as shown herein for the first time, using energy to activate the neuroimmune anti-inflammatory pathway (e.g., including the vagus nerve) has been observed to be therapeutically beneficial in clinical trial subjects that have previously not been adequately treated by TNF inhibitors.

The application of energy to activate the neuroimmune anti-inflammatory pathway includes applying energy to nerves other than the vagus nerve, such as the splenic nerve, sacral nerve, etc. and is herein described as being similarly effective. For example, stimulating the splenic nerve is known to cause the release of norepinephrine which acts on adrenergic receptors on immune cells in the spleen to decrease the production and release of TNF (Kees et al. (2003), "Via beta-adrenoceptors, stimulation of extrasplenic sympathetic nerve fibers inhibits lipopolysaccharide-induced TNF secretion in perfused rat spleen," *J Neuroimmunol* 145(1-2): 77-85). In addition, norepinephrine also acts on adrenergic receptors within a subset of T cells and B cells that result in production and release of acetylcholine by those cells (Rosas-Ballina et al (2011), "Acetylcholine-synthesizing T cells relay neural signals in a vagus nerve circuit," *Science* 334(6052): 98-101). The acetylcholine then acts through the alpha 7 nicotinic acetylcholine receptor on nerves and other immune cells to decrease the production and release of TNF (Vida et al. (2011), "alpha7-cholinergic receptor mediates vagal induction of splenic norepinephrine," *J Immunol* 186(7): 4340-4346). The splenic nerve is activated by vagus nerve stimulation causing reduction in TNF production and release (Olofsson et al. (2015). "Single-pulse and unidirectional electrical activation of the cervical vagus nerve reduces tumor necrosis factor in endotoxemia." Bioelectronic Medicine: 37-42). Based on the current understanding of the neuroimmune anti-inflammatory pathway, it would be expected that a patient who has previously not had an adequate clinical response to TNF inhibitors would not be very sensitive to alternative treatments that also block TNF signaling such as neuroimmune anti-inflammatory pathway activation. It is therefore quite surprising that, as described herein, using energy to activate the vagus nerve and thereby activating the splenic nerve has been observed to be therapeutically beneficial in clinical trial subjects that have previously not been adequately treated by TNF inhibitors.

Similar results would be expected for applying energy to the neuroimmune anti-inflammatory pathway via the sacral nerve, which is part of the parasympathetic nervous system. It has been demonstrated that stimulating the sacral nerve with energy can lead to activation of the vagus nerve. This leads to release of neurotransmitters that act on immunocytes thereby decreasing the production and release of TNF (Pasricha et al. (2020), "Sacral nerve stimulation prompts vagally-mediated amelioration of rodent colitis," *Physiol Rep* 8(1): e14294). One would think that a patient who has previously not had an adequate clinical response to TNF inhibitors would not be very sensitive to alternative treatments that also block TNF signaling. Again, it is therefore surprising that, as described herein, using energy to activate the sacral nerve (and therefore the vagus nerve) would be therapeutically beneficial in subjects that have previously not been adequately treated by TNF-inhibitors.

Similarly, the application of energy to activate the neuroimmune anti-inflammatory pathway via the tibial and peronial nerves that branch off at the ST36 acupoint would also not be expected to be effective in subjects that have previously not been adequately treated by TNF-inhibitors (Liu et al. (2021), "A neuroanatomical basis for electroacupuncture to drive the vagal-adrenal axis," *Nature* 598(7882): 641-645). This leads to release of neurotransmitters that act on immunocytes thereby decreasing the production and release of TNF. It would therefore be expected that a patient who has previously not had an adequate clinical response to TNF inhibitors would not respond to alternative treatments that also block TNF signaling. It is therefore quite surprising that, as described herein, using energy applied to these nerves, which is known to also activate the vagus nerve, has been observed to be therapeutically beneficial in clinical trial subjects that have previously stopped responding (or simply did not respond) to treatment by TNF-inhibitors.

Although nerve stimulation for treatment of inflammatory conditions has previously been described, nerve stimulation specifically in patient's that have failed to adequately respond or that are intolerant to a TNF inhibitor therapy has not been suggested. As described herein, and illustrated in the clinical examples below, the application of energy to activate the neuroimmune anti-inflammatory pathway in patient's that have failed to adequately respond or that are intolerant to a TNF inhibitor drug therapy is not only effective but may also re-sensitize these same patients to the same TNF inhibitor drug to which they were previously non-responsive. For example, nerve stimulation used in conjunction with administration of one or more types of drugs (e.g., TNF inhibitors) are shown herein to be effective. Concurrent with or following the application of energy to activate the neuroimmune anti-inflammatory pathway may also reduce the required dosage of the TNF inhibitor and/or the necessary frequency of administration of the drug(s) to achieve a therapeutically beneficial effect. In some cases, the nerve stimulation can replace the administration of the drug(s).

The apparatuses and methods described herein may include applying energy to activate the neuroimmune anti-inflammatory pathway at a level necessary to modulate a subject's neuroimmune reflexes. For example, the nerve stimulation may modulate the cholinergic anti-inflammatory pathway (CAP), for example, by modulating cytokine release. The neurostimulation may be administered through the use of implanted neural stimulation devices (microstimulators) and/or transcutaneous electrical nerve stimulation (TENS) devices. The treatment and management of symptoms manifested from the onset of disease (e.g., inflammatory disease) may be based upon modulating neuroimmune reflexes (e.g., the CAP). The CAP pathway normally maintains precise restraint of the circulating immune cells. As used herein, the CAP is a reflex that utilizes cholinergic nerve signals traveling via nerves between the brain, chemoreceptors, and the reticuloendothelial system (e.g., spleen, liver). Local release of pro-inflammatory cytokines (e.g., tumor necrosis factor or TNF) from resident immune cells is inhibited by the efferent, or indirectly by afferent nerve signals. Modulation of the CAP causes important changes in the function and microenvironment of the spleen, liver and other reticuloendothelial organs. Leukocytes which circulate systemically become "educated" as they traverse the liver and spleen are thereby functionally down regulated by the affected environment of the reticuloendothelial system. This effect can potentially occur even in the absence of an inflammatory condition.

Remote inflammation may then be dampened by down-regulated cytokine levels. Stimulation of one or more nerves (e.g., vagus nerve, sacral nerve, and/or splenic nerve) of the neuroimmune anti-inflammatory pathway with a specific regiment of energy (e.g., electrical pulses, thermal energy, mechanical energy, etc.) regulates production of pro-inflammatory cytokines. In-turn, the down regulation of these cytokines may reduce localized inflammation in joints and other organs of patients with autoimmune and inflammatory disorders.

Any of a number of nerves of the neuroimmune anti-inflammatory pathway may be stimulated to activate the cholinergic anti-inflammatory pathway. In some examples, the vagus nerve, the splenic nerve and/or the sacral nerve is/are stimulated. In the case of the vagus nerve, any of a number of regions of the vagus nerve, including nuclei and/or branches of the vagus nerve, may be stimulated. In some examples, one or more of a pharyngeal nerve branch, superior laryngeal nerve branch, superior cervical nerve branch, inferior cervical nerve branch, recurrent laryngeal nerve branch, thoracic nerve branch, branches to the pulmonary plexus, branches to the esophageal plexus, anterior vagal trunk, posterior vagal trunk, dorsal nucleus, nucleus ambiguous, solitary nucleus, and/or spinal trigeminal nucleus of the vagus nerve is/are stimulated. In some specific examples, the efferent vagus nerve is stimulated. In some specific examples, the cervical vagus nerve is stimulated.

The methods and apparatuses described herein may be effective in reducing inflammatory symptoms associated with any of a number of inflammatory disorders and/or autoimmune disorders, including arthritis (e.g., rheumatoid, bursitis, gouty arthritis, and/or polymyalgia rheumatic), inflammatory bowel disease (e.g., Crohn's disease and/or ulcerative colitis), multiple sclerosis, coeliac disease, systemic lupus erythematosus, aplastic anemia, myocarditis, spondyloarthritis, inflammatory myositis, alopecia, psoriasis, hay fever, atherosclerosis, asthma, chronic inflammation, chronic prostatitis, glomerulonephritis, nephritis, pelvic inflammatory disease, reperfusion injury, transplant rejection, vasculitis, and/or myocarditis.

Activation of the cholinergic anti-inflammatory pathway can involve electrical nerve stimulation, pharmacological nerve stimulation, and/or or physical nerve stimulation.

Electrical nerve stimulation involves administering of electrical current to the patient to cause sufficient stimulation of one or more nerves to activate the cholinergic anti-inflammatory pathway. The electrical stimulation may be by an implanted device and/or by a transcutaneous device. Pharmacological nerve stimulation involves administering one or more pharmacological agents to the patient sufficient to cause stimulation of one or more nerves. Mechanical nerve stimulation involves one or more mechanical interventions (e.g., acupuncture, focused ultrasound) to cause stimulation of one or more nerves. In some examples, activation of the cholinergic anti-inflammatory pathway involves a combination of electrical, pharmacological and/or physical activation. The electrical, pharmacological and/or physical interventions maybe performed simultaneously or serially during a treatment regimen.

A nerve stimulation treatment regimen can include administering a number of electrical stimulations over a period of time. In some cases, the intensity (which is associated with the electric current) of stimulations can be controlled by the user. In some cases, the frequency of electrical stimulations can be applied upon demand as controlled by the user. For example, a device (e.g., implanted microstimulator or TENS device) can include a control for a user to apply a dose of electrical stimulation when needed. In some examples, a control can be used to increase or decrease an intensity (e.g., current) of the electrical stimulations. In some cases, the intensity and frequency of the electrical stimulations are predetermined. For example, a device (e.g., implanted microstimulator or TENS device) can be programmed to apply electrical stimulation at a prescribed intensity and/or at a prescribed frequency. In one example, the device can be programmed to apply electrical stimulation at a relatively high intensity and/or frequency during times of the day/week/month that are determined to be associated with high pain, and to apply electrical stimulation at a relatively low intensity and/or frequency during times of the day/week/month that are determined to be associated with low pain.

Electrical nerve stimulation may be applied by one or more electrodes of an implanted device (e.g., implanted neurostimulator). The parameters of electrical stimulation may vary depending on the patient, and type and severity of the condition. In some examples, an electrical stimulus of 50 mA or less (e.g., 40 mA or less, 30 mA or less, 20 mA or less, 15 mA or less, 10 mA or less, 2 mA or less, etc.) is used. In some examples, the electrical stimulus can be between about 0.05 to 5 mA, or 0.05 to 10 mA, or 0.05 to 15 mA, 0.05 to 20 mA, or 0.05 to 25 mA or 0.05 to 50 mA. In some examples, the current applied may be less than between about 20 μA to 200 μA against the nerve, or from 200 μA and 2 mA transvenously. In some examples, the charge applied may between about 0.2 nanocoulombs to 1 kilocoulomb.

Transcutaneous electrical nerve stimulation (TENS) can be provided by an electrical stimulation device having at least one electrode that can be placed on the patient's skin. A control or signal generator can deliver the electrical signal stimulus through the electrode. In some examples, the electrical stimulus can be between about 0.05 to 10 mA, or 0.05 to 15 mA, or 0.05 to 20 mA, or 0.05 to 25 mA, or 0.05 to 50 mA. The pulse width can be between about 100 and 1,000 μS. The pulse frequency can be between about 1 and 50 Hz, and the stimulus duration can be between about 1 second and 24 hours. In some examples, the daily charge delivered at about 0.2 nanocoulombs to 1 kilocoulomb per day.

In some examples, dose intensity may be set to within a therapy window. The therapy window is defined by a lower limit of current necessary to trigger an anti-inflammatory response, and an upper limit of current at which the patient feels uncomfortable. The lower limit is referred to as the Threshold (T), and the highest level at which the subject is still comfortable is referred to as the Upper Comfort Level (UCL). The T and/or the UCL may be determined by administering test stimulations to the patient. The testing can involve applying stimulations at progressively increasing (or decreasing) current. The T current can be associated with the current when the patient first experiences perception of stimulation. The UCL current can be associated with the current applied prior to when the patient first feels discomfort.

The clinical results described herein may be measured according to standard clinical measurement tools and techniques. For example, the DAS28-CRP is modified version of the original Disease Activity Score (DAS) for rheumatoid arthritis assessment, which eliminates some of the variables and replaces the erythrocyte sedimentation rate (ESR) with the C-reactive protein (CRP). The Crohn's Disease Activity Index (CDAI) a tool used to quantify the symptoms of patients with Crohn's Disease. Clinical disease activity metrics used for RA (e.g., DAS28-CRP/ESR or CDAI) may be used to determine whether a subject has high disease activity, moderate disease activity, low disease activity, or is in remission. The clinical studies described herein may be implemented according to a treat-to-target approach protocol where a low disease activity state (or remission) is the target.

Biological Drugs

Figure 1:
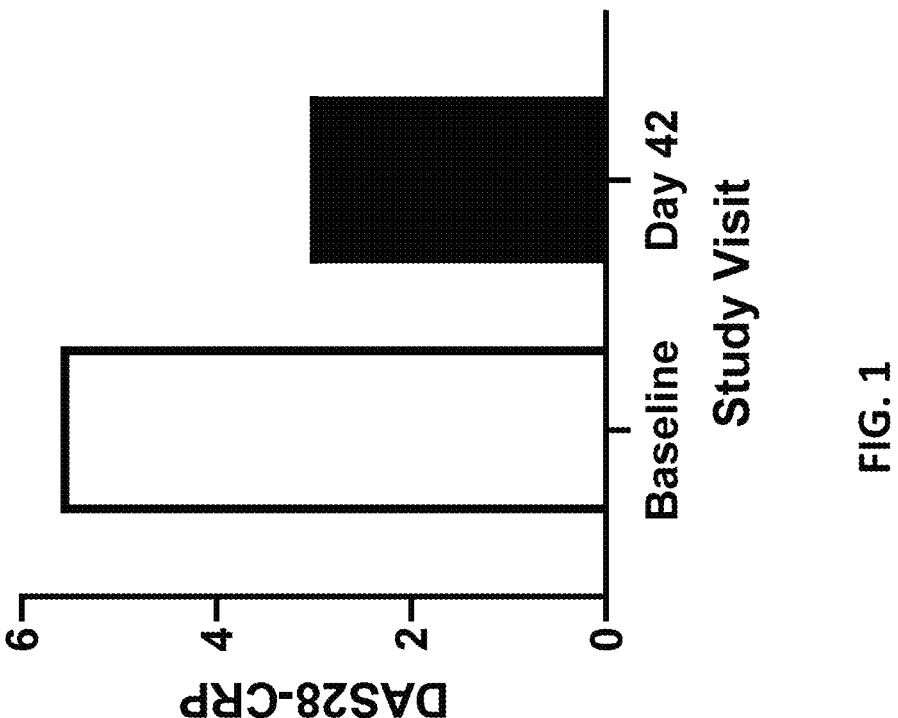

Biopharmaceuticals (also referred to as biologics or biological drugs) generally refer to pharmaceutical drugs manufactured in, extracted from, or semisynthesized from biological sources. Although various biologics have been shown to reduce the signs and symptoms of rheumatoid arthritis, their effectiveness may vary depending on the type of biologic and the patient, and their effectiveness may wane over time. FIGS. 1-2 show clinical results of administration of nerve stimulation therapy without administration of a biologic. In all cases, the subjects were previously found to be insufficiently treated by a biological therapy, specifically a TNF inhibitor. For example, the subjects may have failed to achieve or maintain at least a low disease activity as a target of therapy using the biological therapy alone.

FIG. 1 shows results of clinical studies involving nerve stimulation treatment in RA subjects who had previously been given biologic therapies. The graph of FIG. 1 shows the change in DAS28-CRP from baseline monitored over a period of time (42 day period). The study visit baseline corresponds to the screening visit and study entry. The VNS included electrical stimulation by a microstimulator device implanted in the patient, where patient was given stimulation with simulation intensity was no greater than an Upper Comfort Level (UCL), as described herein. A treatment that results in a change in the DAS28-CRP that is greater than the minimal clinically important difference (MCID) is deemed to have an implication in clinical management. The subject had initially tried and either did not respond or lost response to biological drugs, including anti TNF prior to enrolling into the study Clinical results were recorded as DAS28-CRP scores and associated with "high disease," "moderate disease," "low disease," and "remission" states.

FIG. 1 shows clinical results for a subject with a history of TNF targeted biologic refractory rheumatoid arthritis who enrolled in the VNS study following lack of clinical response to biologics. Specifically, the subject had prior history of being treated and then ceasing treatment of the anti-TNF biologics adalimumab and infliximab and etanercept due to ineffectiveness. (This subject had also not insufficient clinical effectiveness to abatacept.) This subject was a 37 year-old female at baseline, in highly active clinical disease. As shown, the subject had a drop in DAS28-CRP of 2.56 after 42 days of vagus nerve stimulation, representing a clinically meaningful response. These results indicate that therapy with activation of neuro-immune reflexes had efficacy in rheumatoid arthritis despite the subject's previous exposure to and lack of efficacy to a TNF targeted biologic.

FIG. 2 shows clinical results for a subject with a history of TNF targeted biologic refractory Crohn's disease who enrolled in the VNS study following lack of clinical response to biologics. Specifically, the subject had prior history of being treated and then ceasing treatment of the anti-TNF biologics adalimumab and infliximab, golimumab, and etanercept due to ineffectiveness. (This subject had also not insufficient clinical effectiveness to ustekinumab and vedolizumab.) This subject was a 39 year-old female at baseline, in moderately active clinical disease. As shown, the subject achieved clinical remission and had a drop in CDAI of 125 after 16 weeks of vagus nerve stimulation, representing a clinically meaningful response. These results indicate that therapy with activation of neuro-immune reflexes had efficacy in Crohn's disease despite the subject's previous exposure to and lack of efficacy to a TNF targeted biologic.

Targeted Synthetic Drugs

In general, targeted synthetic DMARDs (tsDMARDs) are drugs that are developed to target a particular molecular structure. Janus kinase (JAK) inhibitors are a class of tsDMARD that target inhibition of one or more of the JAK family of enzymes (JAK1, JAK2, JAK3, TYK2), thereby interfering with the JAK-STAT signaling pathway.

Figure 3:
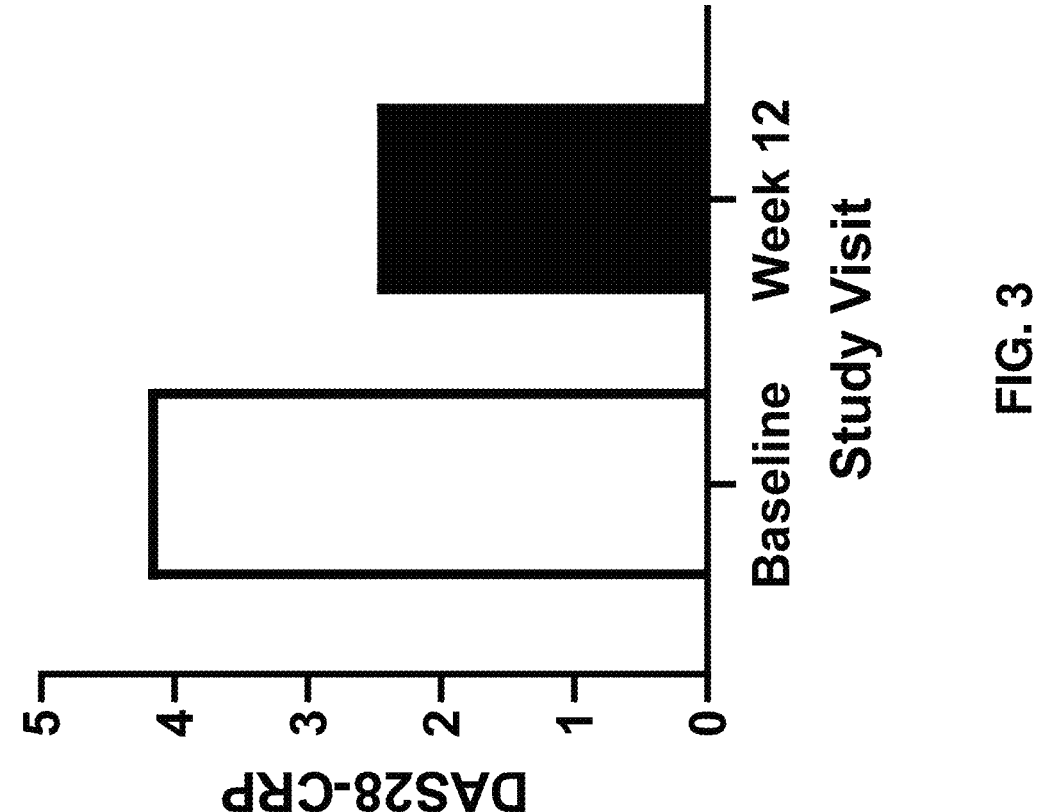

FIG. 3 shows clinical results for a subject with a history of tsDMARD refractory rheumatoid arthritis who enrolled in the VNS study following lack of clinical response to biologics. Specifically, the subject had prior history of being treated and then ceasing treatment of the JAK inhibitor tofacitinib due to ineffectiveness. (This subject had also not insufficient clinical effectiveness to biologics targeting TNF; infliximab, IL-6; tocilizumab, and CTLA-4; abatacept.) This subject was a 47 year-old female at baseline, in highly active clinical disease. As shown, the subject had a drop in DAS28-CRP of 1.72 after 12 weeks of vagus nerve stimulation, representing a clinically meaningful response. These results indicate that therapy with activation of neuro-immune reflexes had efficacy in rheumatoid arthritis despite the subject's previous exposure to and lack of efficacy to a JAK inhibitor.

Although the examples described above involve the use of standard disease activity scores (DAS28-CRP and CDAI) for determining a disease activity state in a subject, other methods may alternatively or additionally be used. For example, a disease state of a subject may alternatively or additionally be quantified by measuring one or more biomarkers. In some cases, the biomarkers may be measured in the blood, urine and/or soft tissue. In some cases, the biomarkers may be patient reported outcomes, quality of life metrics, and/or metrics related to activity or gait. The biomarkers may include proteins, antibodies and/or genetic biomarkers. The type of biomarker being monitored may depend on the particular condition. Example biomarkers may include C-reactive protein, IL6, SAA, rheumatoid factor, autoantibodies against citrullinated proteins erythrocyte sedimentation rate, and/or fecal calprotectin. The biomarker(s) may be measured at various times. For example, the biomarker(s) may be measured before, during and/or after a treatment (e.g., neurostimulation and biologic co-treatment).

Any of the nerve stimulation methods described herein may be combined with one or more immunosuppressant and/or anti-inflammatory drugs. The immunosuppressant drug may include one or more biological drugs (e.g., biological DMARDs), one or more targeted synthetic drugs (e.g., targeted synthetic DMARDs), and/or one or more conventional drugs (e.g., conventional DMARDs). Example biological drugs may include rituximab, tocilizumab, etanercept, abatacept, adalimumab, infliximab, anakinra, certolizumab, certolizumab pegol, golimumab, ixekizumab, natalizumab, secukinumab, ustekinumab, sarilumab, vedolizumab, and/or biosimilars of any of these drugs. Example targeted synthetic drugs may include one or more JAK inhibitors and/or one or more phosphodiesterase 4 (PDE4) inhibitors. Example JAK inhibitors may include upadacitinib, tofacitinib, baricitinib, and/or filgotinib. Example PDE4 inhibitors may include apremilast, roflumilast, apremilast, and/or crisaborole. Example conventional drugs may include ciclosporin, cyclophosphamide, hydroxychloroquine, methotrexate, leflunomide, mycophenolate and/or sulfasalazine. Other possible drugs may include azathioprine, chloroquine, calcineurin inhibitors (e.g., ciclosporin and/or prednisolone), D-penicillamine and/or minocycline. The drugs may include brand-named drugs and/or generic drugs. The drugs may include approved drugs (e.g., by a government agency) and/or pre-approved drugs.

Any of the nerve stimulation and DMARD co-therapies described herein may be administered in combination with one or more additional drugs. Such additional drugs may include one or more corticosteroids (e.g., prednisone, dexamethasone, and/or prednisolone), mTOR inhibitors (e.g., sirolimus, and/or everolimus), IMDH inhibitors (e.g., axathioprine, leflunomide, and/or mycophenolate), monoclonal antibodies (e.g., basiliximab, and/or daclizumab), nonsteroidal anti-inflammatory drugs (NSAID), and/or quinolines (e.g., hydroxychloroquine).

In some examples, the nerve stimulation apparatuses (e.g., microstimulators) may be configured to be inserted or implanted into the body. The apparatus may include a stimulation applicator (also referred to as simply a stimulator) that may be a mechanical and/or electrical stimulator. A mechanical stimulator may be a piezoelectric driver that may vibrate and/or apply pressure to the tissue, including to the nerve, in the nerve treatment parameters, such as mechanical stimulation of the nerve at between 1-2 kHz for a treatment time (e.g., between 1 ms and 5 minutes, e.g., 10 ms-10 sec, etc.). Alternatively or additionally, the stimulation applicator may be an electrical stimulation applicator and may include one or more (e.g., two or more) electrodes configured to apply electrical stimulation to the nerve. For example, electrical stimulation of about 0.1 mA to 10 mA (e.g., between 1 mA-5 mA), at a frequency of between about 1 Hz and about 2 kHz (e.g., between about 1-100 Hz), where the pulses applied have a pulse width of between about (50-500 μsec, e.g., between about 100-300 μsec) or a daily charge delivered at about 0.2 nanocoulombs to 1 kilocoulomb per day. The controller may be configured to enforce an 'off-time' following a nerve treatment dose of between about 10 minute and 12 hours (e.g., between about 2 hours and 10 hours, between about 3 hours and 6 hours, at least 2 hours, at least 3 hours, at least 4 hours, at least 5 hours, at least 6 hours, etc.). For example, the stimulator may include an electrode configured to apply electrical energy to the nerve.

In some variations, the apparatus is configured to apply nerve stimulation treatment to the patient in which the nerve stimulation is electrical stimulation. For example, the nerve stimulation treatment may include the application of electrical energy at between about 1-100 Hz (e.g., between about 1-50 Hz, between about 1-20 Hz, between about 5-30 Hz, between about 5-15 Hz, approximately 5 Hz, approximately 10 Hz, approximately 15 Hz, etc.). The energy may have a peak amplitude of between about 0.1 mA and about 2 mA (e.g., between about 0.2 mA and about 1.8 mA, between about 0.5 mA and about 1.5 mA, between about 0.5 mA and about 1 mA, between about 0.1 mA and about 1 mA, approximately 0.5 mA, approximately 0.75 mA, approximately 1 mA, etc.). Alternatively, the applied energy may have an average amplitude of between about 0.1 mA and about 2 mA (e.g., between about 0.2 mA and about 1.8 mA, between about 0.5 mA and about 1.5 mA, between about 0.5 mA and about 1 mA, between about 0.1 mA and about 1 mA, approximately 0.5 mA, approximately 0.75 mA, approximately 1 mA, etc.) or a daily charge delivered at about 0.2 nanocoulombs to 1 kilocoulomb per day. The applied energy is typically pulsed, and may be pulsed square waves, sinusoidal waves, triangular waves, etc. The applied energy may be biphasic or monophasic. For example, the applied energy maybe biphasic. The applied nerve stimulation treatment may be a constant biphasic pulse train having a frequency of between 1-100 Hz (e.g., 10 Hz) and a peak amplitude of between about 0.5 mA and 2 mA (e.g., approximately 0.75 mA). Any of the methods for treatment described herein may be configured to apply this type of nerve stimulation treatment.

Any of the apparatuses (e.g., devices, systems, etc.) described herein may be configured to be implanted on the nerve. Thus, any of these apparatuses may be implanted via a nerve sheath or nerve cuff configured to secure the apparatus onto the nerve and/or prevent movement of the apparatus relative to the nerve and/or insulate the apparatus from other tissues. The implanted apparatus may be implanted in any appropriate location on the nerve. The implant may be a leadless implant that is connected to the nerve (see, e.g., U.S. Pat. Nos. 8,412,338, 8,612,002, 8,886,339, and 8,788,034, each of which is herein incorporated by reference in its entirety). For example, any of these apparatuses may include a nerve cuff configured to secure the stimulator to the nerve. Alternatively, any of these apparatuses may include a lead connecting the microstimulator and/or other components to the stimulation applicator on/around the nerve via one or more leads.

Any of these apparatuses may be configured to apply nerve stimulation treatment including a low duty-cycle electrical stimulation of between about 0.25 mA and about 5 mA to the nerve for less than about 2 minutes. The apparatus may be configured to provide an off-time of at least x minutes/hours (e.g., 10 minutes, 20 minutes, 30 minutes, 40 minutes, 60 minutes, 2 hours, 3 hours, 4 hours, etc.).

Systems for electrically stimulating one or more nerves to treat chronic inflammation may include an implantable, wireless microstimulator and an external charging device. In some examples the system also includes a controller such as a "prescription pad" that helps control and regulate the dose delivered by the system. The microstimulator may be secured in position using a securing device (which may be referred to as a "POD") to hold the microstimulator in position around or adjacent to a nerve. These microstimulators are designed and adapted for treatment of chronic inflammation and may be configured specifically for such use. Thus, an implantable microstimulator may be small, and adapted for the low duty-cycle stimulation to modulate inflammation. For example, the implantable microstimulator may hold a relatively small amount of power over weeks or even months and discharge it at a rate sufficient to modulate the anti-inflammatory pathway without significantly depressing heart rate or triggering any number of unwanted effects from the nerve.

When configured to sub-diaphragmatic vagus nerve stimulation, the apparatuses may be preferred over cervical vagus nerve application. In such examples, a single implant (e.g., single leadless microstimulator, including those described herein) may be adapted for sub-diaphragmatic implantation. Such implants may be adapted for sub-diaphragmatic implantation by including one or more features including: a location and/or orientation emitter (configured to emit a wireless signal indicating implant location and orientation, particularly of an inductive coil(s) within the implant), multiple inductive coils for communication (including charging), a controller adapted to deliver a large stimulation dose (e.g., a single pulse or bursts of pulses having between 6.5 and 20 V for a dose duration of between 0.1 second and 1000 seconds (e.g., between 0.3 s and 500 s, between 0.5 s and 100 s, etc.), followed by a low-power, "off" time during which the implant may not apply stimulation; this off time may be between 1 hour and 48 hours (e.g., between 2 hours and 48 hours, between 3 hours and 48 hours, between 4 hours and 36 hours, greater than 2 hours, greater than 3 hours, greater than 4 hours, etc.), or a daily charge delivered at about 0.2 nanocoulombs to 1 kilocoulomb/day.

Janus Kinase (JAK) inhibition

As mentioned above, in addition to patient's that failed TNF inhibition, similar and significant results were seen in patients that had previously seen to be intolerant to or had failed to adequately respond to Janus Kinase (JAK) inhibition. In general, stimulating the neuroimmune anti-inflammatory pathway (e.g., the vagus nerve and/or the splenic nerve) with enough energy to depolarize the neurons and cause an action potential activates the neuroimmune pathway. These neuroimmune pathway may utilize both nerves and immune cells, using neurotransmitters to communicate (Tracey (2002)). These reflexes include, but are not limited to, the cholinergic anti-inflammatory pathway and the intestinal cholinergic anti-inflammatory pathway. The cholinergic anti-inflammatory pathway involves the splenic nerve and the spleen (Olofsson et al. (2012)) while the intestinal cholinergic anti-inflammatory pathway is spleen independent (Caravaca et al. (2022)). When neurotransmitters, specifically acetylcholine, is released in the tissues, it binds through the alpha 7 nicotinic acetylcholine receptor on immune cells to downregulate proinflammatory cytokines through modulating the JAK/STAT pathways (de Jonge et al. (2005), "Stimulation of the vagus nerve attenuates macrophage activation by activating the Jak2-STAT3 signaling pathway," Nat Immunol 6(8): 844-851; and Yang et al. (2015), "Acetylcholine Inhibits LPS-Induced MMP-9 Production and Cell Migration via the alpha7 nAChR-JAK2/STAT3 Pathway in RAW264.7 Cells," Cell Physiol Biochem 36(5): 2025-2038).

JAK/STAT is an important tyrosine kinase and transcription factor, involved in the production of cytokines central to the pathogenesis and pathophysiology of many inflammatory diseases, including rheumatoid arthritis, psoriatic arthritis, Crohn's disease, and ulcerative colitis. Indeed, several therapies targeting the JAK/STAT pathways have been demonstrated effective and are currently marketed for the treatment of these and other diseases. The JAK/STAT pathway has also been implicated in the neuroimmune anti-inflammatory pathway, and one would think that a patient who has previously not had an adequate clinical response to JAK inhibitors would not be very sensitive to alternative treatments that also modulate JAK/STAT signaling. It is therefore quite surprising that using energy to activate the vagus as described above, my result in a therapeutically beneficial effect in clinical trial subjects that have previously not been adequately treated by JAK/STAT pathway inhibitors.

EXAMPLES

In the examples below, patients were treated with an implantable electrical stimulator for applying electrical energy to a nerve of the neuroimmune anti-inflammatory pathway (such as the vagus nerve, the sacral nerve, and/or a splenic nerve). Energy was applied on demand by patients from an implanted device including a pulse generator and one or more electrodes, and patients were monitoring for a year or more. In some cases, patients were given one or more drugs (e.g., TNF inhibitor drugs, etc.) in addition to the electrical stimulation. Electrical stimulation was provided on-demand based on patient control of the frequency of stimulation and simulation intensity was no greater than an Upper Comfort Level (UCL), as described herein. In general in these examples, the charge transfer used was between about 0.15 mC-2.25 mC per treatment "dose" as applied by the patient.

In general, the majority of patients that failed to adequately respond to TNF inhibitor drugs prior to receiving achieved a clinically significant response to electrical stimulation, e.g., treatment resulted in a change in the DAS28-CRP that is greater than the minimal clinically important difference (MCID).

Example 1

For example, in an initial clinical trial, 17 rheumatoid arthritis subjects that had prior exposure to, and exhibited insufficient response or intolerance to, at least 1 TNF inhibitor were implanted with an electrical stimulator and allowed to self-administer a treatment regimen to activate a neuroimmune anti-inflammatory pathway; from this initial study, 9 subjects (69%) achieved ACR20 or greater response, and 8 subjects (62%) had a clinical response that exceeded the DAS28-CRP MID to vagus nerve stimulation.

Subject A3 entered the study as a 59-year-old female with high disease activity. Prior to enrollment this subject was exposed to and had insufficient response or intolerance to adalimumab (TNF inhibitor) and to tocilizumab (IL-6 inhibitor) and to abatacept (CTLA-4). With vagus nerve stimulation alone, this subject did not exceed the DAS28-CRP MID but did achieve ACR20 response after the 6-week primary endpoint and achieved moderate disease activity.

Subject A6 entered the study as a 44-year-old female with high disease activity. Prior to enrollment this subject was exposed to and had insufficient response or intolerance to etanercept and infliximab (TNF inhibitors) and to abatacept (CD20). With vagus nerve stimulation alone, this subject exceeded the DAS28-CRP MID after the 6-week primary endpoint and achieved moderate disease activity and ACR20 response.

Subject A7 entered the study as a 46-year-old female with high disease activity. Prior to enrollment this subject was exposed to and had insufficient response or intolerance to etanercept, adalimumab, and infliximab (TNF inhibitors)

and to tocilizumab (IL-6 inhibitor). With vagus nerve stimulation alone, this subject exceeded the DAS28-CRP MID after the 6-week primary endpoint and achieved low disease activity and ACR50 response.

Subject A8 entered the study as a 37-year-old female with high disease activity. Prior to enrollment this subject was exposed to and had insufficient response or intolerance to etanercept, adalimumab, and infliximab (TNF inhibitors) and to abatacept (CTLA-4). With vagus nerve stimulation alone, this subject exceeded the DAS28-CRP MID after the 6-week primary endpoint and achieved low disease activity and ACR50 response.

Subject A10 entered the study as a 61-year-old female with moderate disease activity. Prior to enrollment this subject was exposed to and had insufficient response or intolerance to etanercept, adalimumab, golimumab, and infliximab (TNF inhibitors) and to tocilizumab (IL-6) and to rituximab (CD20). With vagus nerve stimulation alone, this subject exceeded the DAS28-CRP MID after the 6-week primary endpoint and achieved low disease activity and ACR20 response.

Subject A11 entered the study as a 47-year-old female with high disease activity. Prior to enrollment this subject was exposed to and had insufficient response or intolerance to etanercept and adalimumab (TNF inhibitors) and to tocilizumab (IL-6). With vagus nerve stimulation alone, this subject exceeded the DAS28-CRP MID after the 6-week primary endpoint and achieved moderate disease activity and ACR70 response.

Subject A12 entered the study as a 56-year-old female with high disease activity. Prior to enrollment this subject was exposed to and had insufficient response or intolerance to etanercept and adalimumab (TNF inhibitors) and to tocilizumab (IL-6) and to rituximab (CD20) and to abatacept (CTLA-4). With vagus nerve stimulation alone, this subject exceeded the DAS28-CRP MID after the 6-week primary endpoint but had remained in high disease activity and ACR20 response.

Subject A13 entered the study as a 68-year-old female with high disease activity. Prior to enrollment this subject was exposed to and had insufficient response or intolerance to adalimumab (TNF inhibitor). With vagus nerve stimulation alone, this subject exceeded the DAS28-CRP MID after the 6-week primary endpoint and achieved remission and ACR50 response.

Subject A14 entered the study as a 38-year-old male with high disease activity. Prior to enrollment this subject was exposed to and had insufficient response or intolerance to adalimumab (TNF inhibitor). With vagus nerve stimulation alone, this subject exceeded the DAS28-CRP MID after the 6-week primary endpoint and achieved moderate disease activity and ACR50 response.

Example 2

Although the use of a treatment regimen (e.g., electrical stimulation) to activate a neuroimmune anti-inflammatory pathway in a patient that has failed to adequately respond or is intolerant to a TNF inhibitor therapy may potentiate the TNF inhibitor (e.g., drug) therapy, the use of a TNF inhibitor or other drug was not necessary. For example, Crohn's disease patients that have failed to adequately respond or were intolerant to a TNF inhibitor can respond to nerve stimulation without a biologic or targeted therapy onboard. Of 11 subjects that failed to adequately respond or were intolerant to a TNF inhibitor and which were on vagus nerve stimulation for 16 weeks without a biologic or targeted therapy onboard, 7 of 11 (63%) exceeded the CDAI-100 enhanced MID threshold.

Subject B4 entered the study as a 62-year-old male with moderate disease activity with a CDAI of 292, a SES-CD of 30, and a 5 year history of Crohn's disease. Prior to enrollment this subject was exposed to and had insufficient response or intolerance to infliximab and adalimumab (TNF inhibitors). With vagus nerve stimulation alone, this subject exceeded the enhanced CDAI-100 MID after the 16-week primary endpoint and achieved mild disease activity.

Subject B6 entered the study as a 52-year-old male with moderate disease activity with a CDAI of 270, a SES-CD of 13.7, and a 6 year history of Crohn's disease. Prior to enrollment this subject was exposed to and had insufficient response or intolerance to adalimumab (TNF inhibitor). With vagus nerve stimulation alone, this subject exceeded the enhanced CDAI-100 MID after the 16-week primary endpoint and achieved disease remission.

Subject B7 entered the study as a 25-year-old male with moderate disease activity with a CDAI of 398, a SES-CD of 24.5, and a 6 year history of Crohn's disease. Prior to enrollment this subject was exposed to and had insufficient response or intolerance to infliximab and adalimumab (TNF inhibitors). With vagus nerve stimulation alone, this subject exceeded the enhanced CDAI-100 MID after the 16-week primary endpoint and achieved disease remission.

Subject B8 entered the study as a 31-year-old male with moderate disease activity with a CDAI of 261, a SES-CD of 12, and a 13 year history of Crohn's disease. Prior to enrollment this subject was exposed to and had insufficient response or intolerance to infliximab and adalimumab (TNF inhibitors). With vagus nerve stimulation alone, this subject exceeded the enhanced CDAI-100 MID after the 16-week primary endpoint and achieved disease remission.

Subject B10 entered the study as a 38-year-old female with moderate disease activity with a CDAI of 402, a SES-CD of 13.5, and a 15 year history of Crohn's disease. Prior to enrollment this subject was exposed to and had insufficient response or intolerance to infliximab and adalimumab (TNF inhibitors). With vagus nerve stimulation alone, this subject exceeded the enhanced CDAI-100 MID after the 16-week primary endpoint and remained in moderate disease activity, close to the mild disease cutoff.

Subject B12 entered the study as a 29-year-old female with moderate disease activity with a CDAI of 258, a SES-CD of 16.5, and a 15 year history of Crohn's disease. Prior to enrollment this subject was exposed to and had insufficient response or intolerance to infliximab, adalimumab, etanercept, and golimumab (TNF inhibitors), to ustekinumab (IL12/23 inhibitor), and vedolizumab (α4β7 integrin). With vagus nerve stimulation alone, this subject exceeded the enhanced CDAI-100 MID after the 16-week primary endpoint and achieved disease remission.

Subject B13 entered the study as a 34-year-old male with moderate disease activity with a CDAI of 339, a SES-CD of 16, and a 17 year history of Crohn's disease. Prior to enrollment this subject was exposed to and had insufficient response or intolerance to infliximab and adalimumab (TNF inhibitors). With vagus nerve stimulation alone, this subject exceeded the enhanced CDAI-100 MID after the 16-week primary endpoint and achieved mild disease activity.

Example 3

Patients that failed to adequately respond to a TNF biologic/targeted drug therapy can respond to the addition of nerve stimulation in conjunction with the previously failed biologic or targeted therapy. For example, a subject (Subject C14) that had previously failed to adequately respond to a biological drug and had vagus nerve stimulation added to the maintained drug therapy as co-therapy for 16 weeks and exceeded the CDAI-100 enhanced MID threshold.

Subject C14 entered the study as a 34-year-old male with moderate disease activity with a CDAI of 294, a SES-CD of 24.5, and a 15 year history of Crohn's disease. Prior to enrollment this subject was exposed to and had insufficient response or intolerance to infliximab and adalimumab (TNF inhibitors) and an insufficient response to vedolizumab (α4β7 integrin). Maintaining the steady course of vedolizumab, vagus nerve stimulation was added as a co-therapy. This subject exceeded the enhanced CDAI-100 MID after the 16-week primary endpoint and achieved mild disease activity (borderline remission).

In a pilot clinical trial, many of the subjects that were exposed to and had insufficient response or intolerance to at least 1 TNF inhibitor (and 1 IL-6 inhibitor), 71% (5 out of 7) subjects achieved ACR20 or greater response.

Example 4

Figure 5A:
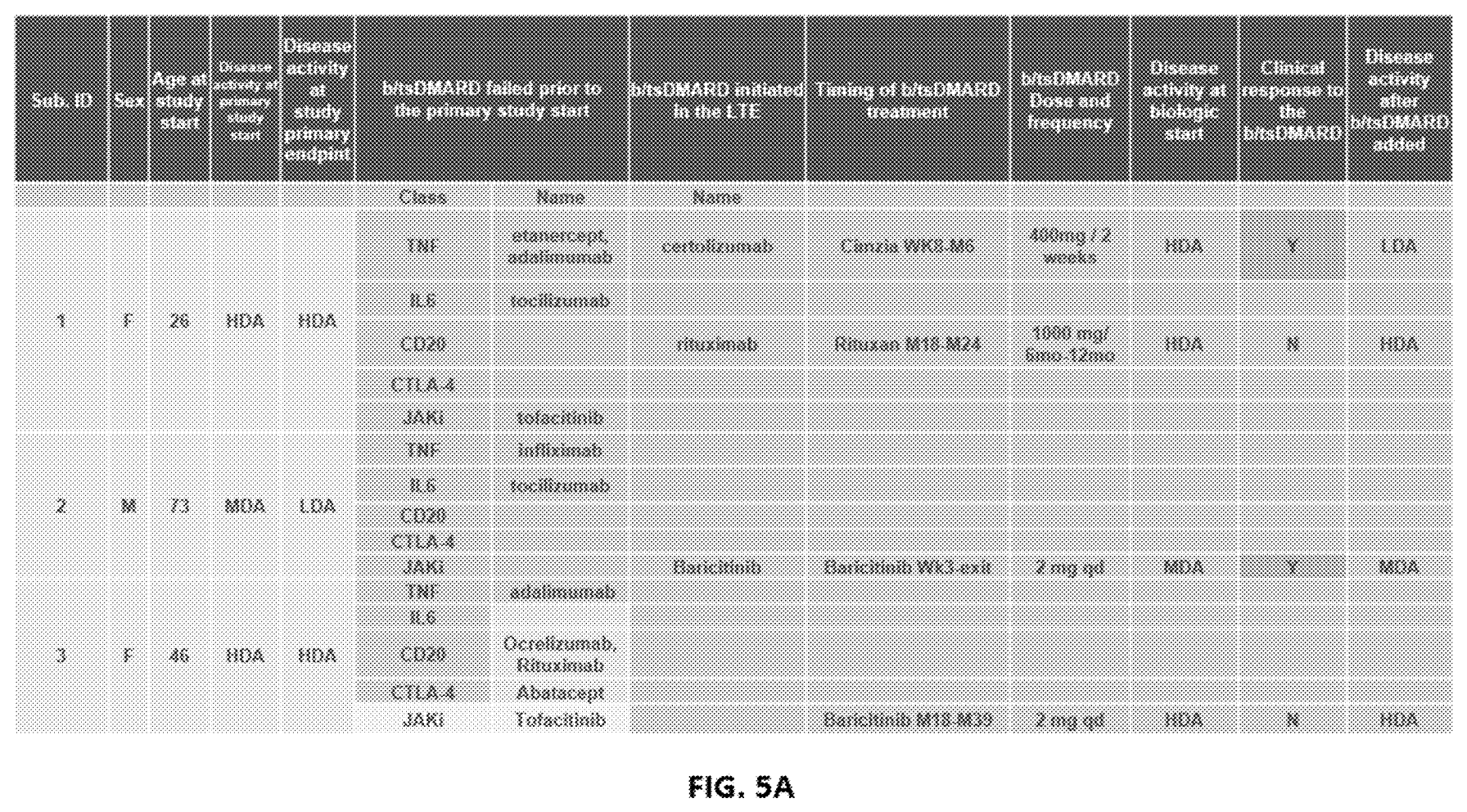

As mentioned above, the methods described herein for treating a patient that had failed or become insensitive to a drug therapy for TNF and/or JAK inhibition surprisingly responded to the combination of a treatment regimen to activate a neuroimmune anti-inflammatory pathway and the same or a similar TNF and/or JAK inhibitor. For example, FIGS. 4A-4B and 5A-5C summarize patient data for patients that were treated as described above. For example, FIGS. 4A-4B show subjects that were treated as describe above, an lists the biologics (shown by class and by name) that were failed prior to implantation of an energy application device to apply energy to activate a neuroimmune anti-inflammatory pathway, as well as biologics that were given in combination with the application of energy during the observed period (e.g., typically greater than 1 year), and an indicator of the response and disease activity (R=remission, LDA=low disease activity, MDA=moderate disease activity, HDA=high disease activity). In FIGS. 5A-5C similar data is provided, showing biologics failed, timing or biologics given in combination with an energy treatment, and patient response (as well as disease activity).

As discussed above, significant responses, e.g., recovery of efficacy of the biologic, for a majority of patients when previously failed biologics or tsDMARDs were provided in combination with the application of energy to activate a neuroimmune anti-inflammatory pathway.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one example, the features and elements so described or shown can apply to other examples.

It will also be appreciated by those of skill in the art that references to a structure or feature that is disposed "adjacent" another feature may have portions that overlap or underlie the adjacent feature.

Terminology used herein is for the purpose of describing particular examples only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and examples such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative examples are described above, any of a number of changes may be made to various examples without departing from the scope of the invention as described by the claims. For example, the order in which various described method steps are performed may often be changed in alternative examples, and in other alternative examples one or more method steps may be skipped altogether. Optional features of various device and system examples may be included in some examples and not in others. Therefore, the foregoing description is provided primarily for exemplary purposes and should not be interpreted to limit the scope of the invention as it is set forth in the claims.

The examples and illustrations included herein show, by way of illustration and not of limitation, specific examples in which the subject matter may be practiced. As mentioned, other examples may be utilized and derived there from, such that structural and logical substitutions and changes may be made without departing from the scope of this disclosure. Such examples of the inventive subject matter may be referred to herein individually or collectively by the term "invention" merely for convenience and without intending to voluntarily limit the scope of this application to any single invention or inventive concept, if more than one is, in fact, disclosed. Thus, although specific examples have been illustrated and described herein, any arrangement calculated to achieve the same purpose may be substituted for the specific examples shown. This disclosure is intended to cover any and all adaptations or examples of various examples. Combinations of the above examples, and other examples not specifically described herein, will be apparent to those of skill in the art upon reviewing the above description.

What is claimed is:

1. A method of reducing inflammation in a patient that is intolerant to or has failed to respond to Tumor Necrosis Factor ("TNF") inhibition, the method comprising:

identifying that the patient has failed to respond to TNF inhibitor therapy comprising a drug that inhibits TNF; and administering a treatment regimen by applying electrical energy to activate a neuroimmune anti-inflammatory pathway in the patient to restore the efficacy of the drug that inhibits TNF; and treating the patient with the drug that inhibits TNF concurrent with or following restoration of the efficacy of the drug that inhibits TNF.

2. The method of claim 1, further comprising continuing to deliver the drug at a tapered dose that is less than a prior dose.

3. The method of claim 1, wherein administering the treatment regimen comprises applying energy to one or more nerve targets.

4. The method of claim 1, wherein applying energy comprises applying electrical energy.

5. The method of claim 1, wherein activating the neuroimmune anti-inflammatory pathway in the patient comprises administering the treatment regimen to one or more of: a vagus nerve, a trigeminal nerve, a glossopharyngeal nerve, an optic nerve, or a facial nerve.

6. The method of claim 1, wherein the TNF inhibitor therapy is one or more of: etanercept, adalimumab, certolizumab pegol, infliximab, golimumab, and biosimilars thereof.

7. The method of claim 1, wherein the patient has an immune or inflammatory disorder.

8. The method of claim 7, wherein the immune or inflammatory disorder is one of: rheumatoid arthritis and psoriatic arthritis.

9. The method of claim 4, wherein applying electrical energy comprises applying a plurality of electrical stimulations each having a current no greater than an upper comfort level.

10. The method of claim 9, further comprising determining the upper comfort level by: administering test stimulations at progressively increasing currents; and associating the upper comfort level to the current at which the patient first feels discomfort.

11. The method of claim 4, wherein applying electrical energy comprises applying a charge ranging from 0.2 nanocoulombs and 5 kilocoulomb.

12. The method of claim 1, wherein applying electrical energy to activate the neuroimmune anti-inflammatory pathway in the patient comprises applying electrical energy from an implanted device.

13. The method of claim 12, wherein the implanted device is a leadless device comprising a pulse generator and at least one electrode integrated onto the implanted pulse generator.

14. The method of claim 12, wherein the implanted device is a transcutaneously powered leaded devices with a receiver that receives, stores, and/or transforms energy delivered from outside the body.

15. The method of claim 14, wherein the receiver receives electrical transmission, including nearfield, midfield, and far field transmissions at amplitudes between 0.1 uA-500 mA.

16. The method of claim 14, wherein the receiver receives focused ultrasound energy at frequencies between 0.1-40 MHz and power between 0.01-50 mW/mm2 and pressure between 10-1000 kPa.

17. The method of claim 14, wherein the receiver receives energy through electromagnetic induction between 0.1-500 A/m.

18. A method of reducing inflammation in a patient that is intolerant to or has failed to adequately respond to either Tumor Necrosis Factor ("TNF") inhibition, the method comprising:

identifying that the patient has failed to respond to TNF inhibitor therapy comprising a drug that inhibits TNF;

administering a treatment regimen to restore the efficacy of the drug that inhibits TNF by activating a neuroimmune anti-inflammatory pathway in the patient by applying electrical energy to one of: a vagus nerve, a splenic nerve, a radial nerve, a median nerve, an ulnar nerve, a femoral nerve, a sciatic nerve, a tibial nerve, a splanchnic nerve, a phrenic nerve, a hepatic nerve, a renal nerve, a greater auricular nerve, a lesser occipital nerve, or an auriculotemporal nerve, wherein applying electrical energy comprises applying charge ranging from 0.2 nanocoulombs and 5 kilocoulomb per hour; and treating the patient with the drug that inhibits TNF concurrent with or following restoration of the efficacy of the drug that inhibits TNF.

19. A method of reducing inflammation in a patient that is intolerant to or has failed to respond to Tumor Necrosis Factor ("TNF") inhibition, the method comprising:

identifying that the patient has failed to respond to TNF inhibitor therapy comprising a drug that inhibits TNF;

administering a treatment regimen to activate a neuroimmune anti-inflammatory pathway in the patient to restore the efficacy of the drug that inhibits TNF by applying energy to one of: a vagus nerve, a splenic nerve, a radial nerve, a median nerve, an ulnar nerve, a femoral nerve, a sciatic nerve, a tibial nerve, a splanchnic nerve, a phrenic nerve, a hepatic nerve, a renal nerve, a greater auricular nerve, a lesser occipital nerve, or an auriculotemporal nerve; and administering, concurrent with or after the application of energy to restore the efficacy of the drug, the same drug, or a drug of the same class that inhibits TNF that the patient had previously failed to respond to.

20. The method of claim 1, wherein identifying that the patient has failed to respond to the drug that inhibits TNF comprises identifying that the patient has not attained or maintained low disease activity or remission with the drug that inhibits TNF, wherein the low disease activity or remission is consistent a standard method of quantifying symptoms of the patient including one or more of: Disease Activity Score 28 (DAS28), Crohn's Disease Activity Index (CDAI), Simple Disease Activity Index (SDAI), Routine Assessment of Patient Index Data 3 (RAPID-3), Health Assessment Questionnaire Disability Index (HAQ-DI), and/ or Rheumatoid Arthritis Disease Activity Index (RADAI).

* * * * *